(12) United States Patent
Jacobson et al.

(10) Patent No.: US 7,465,540 B2
(45) Date of Patent: Dec. 16, 2008

(54) MULTIPLE REPORTER READ-OUT FOR BIOASSAYS

(75) Inventors: James W. Jacobson, Leander, TX (US); Jennifer L. Burroughs, Austin, TX (US); Kerry G. Oliver, Austin, TX (US)

(73) Assignee: Luminex Corporation, Austin, TX (US)

( * ) Notice: Subject to any disclaimer, the term of this patent is extended or adjusted under 35 U.S.C. 154(b) by 860 days.

(21) Appl. No.: 09/956,857

(22) Filed: Sep. 21, 2001

(65) Prior Publication Data

US 2003/0054356 A1    Mar. 20, 2003

Related U.S. Application Data

(60) Provisional application No. 60/234,340, filed on Sep. 22, 2000.

(51) Int. Cl.
*C12Q 1/68* (2006.01)
*C12P 19/34* (2006.01)

(52) U.S. Cl. .......................... 435/6; 435/91.2
(58) Field of Classification Search ................ 435/6, 435/91.2; 536/23.1, 24.3
See application file for complete search history.

(56) References Cited

U.S. PATENT DOCUMENTS

| | | | |
|---|---|---|---|
| 3,867,518 A * | 2/1975 | Coffey et al. ................ 424/1 |
| 3,998,526 A | 12/1976 | Katz |
| 4,236,071 A | 11/1980 | Chimenti |
| 4,336,459 A | 6/1982 | Fay |
| 4,337,999 A | 7/1982 | Funada |
| 4,365,153 A | 12/1982 | Seigel et al. |
| 4,374,120 A | 2/1983 | Soini et al. |
| 4,425,029 A | 1/1984 | Funada et al. |
| 4,454,106 A | 6/1984 | Gansow et al. |
| 4,668,049 A | 5/1987 | Canter et al. |
| 4,677,045 A | 6/1987 | Champ et al. |
| 4,818,680 A | 4/1989 | Collins et al. |
| 4,921,280 A | 5/1990 | Jalon |
| 4,968,602 A | 11/1990 | Dattagupta |
| 5,039,206 A | 8/1991 | Wiltshire |
| 5,052,784 A | 10/1991 | Fergason |
| 5,089,387 A | 2/1992 | Tsay et al. |
| 5,104,791 A | 4/1992 | Abbott et al. |
| 5,229,320 A | 7/1993 | Ugajin |
| 5,237,498 A | 8/1993 | Tenma et al. |
| 5,272,056 A | 12/1993 | Burrows et al. |
| 5,283,174 A | 2/1994 | Arnold, Jr. et al. |
| 5,354,873 A | 10/1994 | Allen et al. |
| 5,482,890 A | 1/1996 | Liu et al. |
| 5,492,795 A | 2/1996 | Allen et al. |
| 5,525,516 A | 6/1996 | Krutak et al. |
| 5,622,829 A * | 4/1997 | King et al. .................... 435/6 |
| 5,656,750 A | 8/1997 | Allen et al. |
| 5,736,330 A | 4/1998 | Fulton |
| 5,795,981 A | 8/1998 | Lee et al. |
| 5,853,984 A * | 12/1998 | Davis et al. ................. 435/6 |
| 5,888,885 A | 3/1999 | Xie |
| 5,891,656 A | 4/1999 | Zarling et al. |
| 5,906,670 A | 5/1999 | Dobson et al. |
| 5,925,517 A | 7/1999 | Tyagi et al. |
| 5,952,174 A | 9/1999 | Nikiforov et al. |
| 5,981,180 A | 11/1999 | Chandler et al. |
| 6,027,898 A | 2/2000 | Gjerde et al. |
| 6,046,807 A | 4/2000 | Chandler |
| 6,048,689 A | 4/2000 | Murphy et al. |
| 6,057,107 A | 5/2000 | Fulton |
| 6,059,561 A | 5/2000 | Becker |
| 6,060,237 A | 5/2000 | Nygren et al. |
| 6,063,574 A | 5/2000 | Bronstein et al. |
| 6,287,766 B1 * | 9/2001 | Nolan et al. .................. 435/6 |
| 6,468,751 B1 * | 10/2002 | Adams et al. ................ 435/6 |
| 6,528,057 B1 * | 3/2003 | Ambrus et al. ............. 424/140 |
| 2002/0187470 A1 * | 12/2002 | Casey et al. .................. 435/6 |
| 2003/0215821 A1 * | 11/2003 | Gunderson et al. ........... 435/6 |

FOREIGN PATENT DOCUMENTS

GB    2169403 A    7/1986

(Continued)

OTHER PUBLICATIONS

Iannone et al, Cytometry (Feb. 2000) 39:131-140.*

(Continued)

*Primary Examiner*—Kenneth R. Horlick
(74) *Attorney, Agent, or Firm*—Kevin L. Daffer; Mollie E. Lettang; Daniel McDaniel, LLP

(57) ABSTRACT

A method for detecting a plurality of reactive sites on an analyte, comprising allowing reactants on an addressable microsphere and the reactive sites to react, forming reactant-reactive site pairs distinguishable by fluorescence intensity. The invention also provides a method for detecting a plurality of analytes in a sample using addressable microspheres in combination with one or more reporter reagents. Also provided are a method for determining allele zygosity of a genetic locus having two alleles or more alleles using microparticles, and a method for detecting a plurality of SNPs in nucleic acid molecules. The instant invention also provides a composition comprising an addressable microsphere carrying at least two fluorescent reactants capable of forming reactant-analyte pairs distinguishable by their fluorescence intensity, and kits comprising the inventive composition and a plurality of reporter reagents.

28 Claims, 2 Drawing Sheets

FOREIGN PATENT DOCUMENTS

| | | | |
|---|---|---|---|
| WO | WO 91/00926 | | 1/1991 |
| WO | WO 97/14028 | * | 4/1997 |
| WO | WO 98/59233 | | 12/1998 |
| WO | WO 99/19515 | | 4/1999 |
| WO | WO 99/37814 | | 7/1999 |
| WO | WO 99/36564 | | 10/1999 |
| WO | WO 99/52708 | | 10/1999 |
| WO | WO 99/57955 | | 11/1999 |
| WO | WO 99/58955 | | 11/1999 |
| WO | WO 99/58958 | | 11/1999 |

OTHER PUBLICATIONS

Renner et al, Cytometry (1994) 18:103-108.*

Fulton R J et al: "Advanced multiplexed analysis with the FlowMetrix(TM) system" Clinical Chemistry, American Association for Clinical Chemistry. Winston, US, vol. 43, No. 9, Sep. 1997, pp. 1749-1756.

Smith, P.L., et al., "A Rapid, Sensitive, Multiplexed Assay for Detection of Viral Nucleic Acids Using the Flow Metrix System" *Clinical Chemistry,* vol. 44 No. 9, 1988, pp. 2054-2056.

Kettman, J.R. et al., "Classification and Properties of 64 Multiplexed Microsphere Sets", *Cytometry,* vol. 33, No. 2, Oct. 1, 1998, pp. 234-243.

International Search Report for PCT/US01/29743, filed Sep. 24, 2001.

Tyagi, S. et al., "*Molecular beacons: probes that fluoresce upon hybridization,*" Nat. Biotechnol., vol. 14, 1996: 303-308.

Nickerson, D. A. et al., Proc. Natl. Acad. Sci. (U.S.A.) vol. 87, 1990: 8923-27.

Sprenger et al., Angew. Chem, vol. 79, 1967: 581.

Sprenger et al., Angew. Chem, No. 80, 1968:541.

Maaks et al., Angew. Chem. Intern. Edit., vol. 5, 1966: 888.

Law et al., J. Org. Chem, vol. 57, 1992: 3278.

Matsuo, T., :In situ *visualization of mRNA for basic fibroblast growth factor in living cells.* Biochimica Biophysica Acta, vol. 1379, 1998: 178-84.

Sokol, D.S. et al., "*Real time detection of DNA.RNA hybridization in living cells;*" Proc. Natl. Acad. Sci. U.S.A., vol. 95, 1998: 11538-43.

Tyagi, S. et al., "*Multicolor molecular beacons for allele discrimination.*" Nat. Biotechnol., vol. 16, 1998:49-53.

Leone, G. et al., "*Molecular beacon probes combined with amplification by NASBA enable homogeneous, real-time detections of RNA.*" Nucleic Acids Res., vol. 26, 1998: 2150-55.

Piatek, A.S. et al., "*Molecular beacon sequence analysis for detecting drug resistance in Mycobacterium tuberculosis.*" Nat. Biotechnol., vol. 16, 1998:359-63.

Kostrikis, L.G. et al., "*Spectral genotyping of human alleles.*" Science, vol. 279, 1998: 1228-29.

Giesendorf, B.A. et al., "*Molecular beacons: a new approach for semiautomated mutation analysis.*" Clin. Chem., vol. 44, 1998: 482-86.

Marras, S.A.E. et al., "*Multiplex detection of single-nucleotide variations using molecular beacons.*" Genet. Anal., vol. 14, 1999: 151-56.

Vet, J.A.M. et al., "*Multiplex detection of four pathogenic retroviruses using molecular beacons.*" Proc. Natl. Acad. Sci. U.S. A., vol. 96, 1999: 6394-99.

US 6,066,453, 05/2000, Pinkel et al. (withdrawn)

* cited by examiner

```
                        SEQUENCE LISTING

<160> NUMBER OF SEQ ID NOS: 18

<210> SEQ ID NO 1
<211> LENGTH: 36
<212> TYPE: DNA
<213> ORGANISM: Homo sapiens

<400> SEQUENCE: 1
cggtctggaa attcttccag aattgatact gaccgg                        36

<210> SEQ ID NO 2
<211> LENGTH: 33
<212> TYPE: DNA
<213> ORGANISM: Homo sapiens

<400> SEQUENCE: 2
cggctatctt taatgtatgg aaaatgagag ccg                           33

<210> SEQ ID NO 3
<211> LENGTH: 17
<212> TYPE: DNA
<213> ORGANISM: Homo sapiens

<400> SEQUENCE: 3
atcttagtgt cccaaat                                             17

<210> SEQ ID NO 4
<211> LENGTH: 17
<212> TYPE: DNA
<213> ORGANISM: Homo sapiens

<400> SEQUENCE: 4
aatcttagag tgtccca                                             17

<210> SEQ ID NO 5
<211> LENGTH: 17
<212> TYPE: DNA
<213> ORGANISM: Homo sapiens

<400> SEQUENCE: 5
cttcacaggg tccttta                                             17

<210> SEQ ID NO 6
<211> LENGTH: 17
<212> TYPE: DNA
<213> ORGANISM: Homo sapiens

<400> SEQUENCE: 6
cttcacagtg tccttta                                             17

<210> SEQ ID NO 7
<211> LENGTH: 17
<212> TYPE: DNA
<213> ORGANISM: Homo sapiens

<400> SEQUENCE: 7
tcaaacaagt taatttc                                             17
```

```
<210> SEQ ID NO 8
<211> LENGTH: 17
<212> TYPE: DNA
<213> ORGANISM: Homo sapiens

<400> SEQUENCE: 8
tcaaacattt taatttc                                                  17

<210> SEQ ID NO 9
<211> LENGTH: 17
<212> TYPE: DNA
<213> ORGANISM: Homo sapiens

<400> SEQUENCE: 9
cagaaaaaaa aggtaga                                                  17

<210> SEQ ID NO 10
<211> LENGTH: 17
<212> TYPE: DNA
<213> ORGANISM: Homo sapiens

<400> SEQUENCE: 10
cagaaaaaaa ggtagat                                                  17

<210> SEQ ID NO 11
<211> LENGTH: 17
<212> TYPE: DNA
<213> ORGANISM: Homo sapiens

<400> SEQUENCE: 11
gtgatgaaca aatgcca                                                  17

<210> SEQ ID NO 12
<211> LENGTH: 17
<212> TYPE: DNA
<213> ORGANISM: Homo sapiens

<400> SEQUENCE: 12
gatgactcac atgatgc                                                  17

<210> SEQ ID NO 13
<211> LENGTH: 17
<212> TYPE: DNA
<213> ORGANISM: Homo sapiens

<400> SEQUENCE: 13
agaaaataag aagagca                                                  17

<210> SEQ ID NO 14
<211> LENGTH: 17
<212> TYPE: DNA
<213> ORGANISM: Homo sapiens

<400> SEQUENCE: 14
agaaaataat caagaag                                                  17

<210> SEQ ID NO 15
<211> LENGTH: 17
<212> TYPE: DNA
<213> ORGANISM: Homo sapiens

<400> SEQUENCE: 15
aggacctgtg aaatcca                                                  17
```

```
<210> SEQ ID NO 16
<211> LENGTH: 17
<212> TYPE: DNA
<213> ORGANISM: Homo sapiens

<400> SEQUENCE: 16
aggacctgcg aaatcca                                                    17

<210> SEQ ID NO 17
<211> LENGTH: 17
<212> TYPE: DNA
<213> ORGANISM: Homo sapiens

<400> SEQUENCE: 17
agagaatccc caggaca                                                    17

<210> SEQ ID NO 18
<211> LENGTH: 17
<212> TYPE: DNA
<213> ORGANISM: Homo sapiens

<400> SEQUENCE: 18
agagaatccc aggacag                                                    17
```

MULTIPLE REPORTER READ-OUT FOR BIOASSAYS

RELATED APPLICATIONS

This application claims priority to U.S. Provisional Application No. 60/234,340, filed Sep. 22, 2000, the disclosure of which is hereby incorporated in its entirety by reference.

FIELD OF THE INVENTION

This invention relates to novel compositions and methods for analyzing, in the same sample, a multitude of analytes and variants thereof. Specifically, the present invention relates to the use of solid phase, e.g., microsphere-based multiplexed assay in flowcytometry. The invention utilizes fluorescently addressable sets of microspheres which carry a mixture of two or more analyte-specific reactants, and at least two analytes can thereby be analyzed simultaneously on microsphere surface.

BACKGROUND OF THE INVENTION

Often, there is a need to perform two or more different assays on the same sample, often in a single vessel and at about the same time. Such assays are known in the art as multiplex or multiplexed assays. Multiplex assays are performed to determine simultaneously the presence/absence or concentration of more than one analyte in the sample being analyzed, or alternatively, several characteristics of a single molecule, such as, the presence of several epitopes on a single protein molecule or identifying alternative alleles of the same gene or nucleic acid sequence.

Detection of nucleotide mutations and polymorphisms is central to the modern science of molecular genetics. For example, allelic discrimination detects different forms of the same gene that differ by nucleotide substitution, insertion, or deletion. In many cases, individuals affected by a given disease display extensive allelic heterogeneity. For example, more than 125 mutations in the human BRCA1 gene have been reported (www.nchgr.nih.gov/dir/lab.sub.—transfer/bic). Mutations in the BRCA1 gene are thought to account for roughly 45% of inherited breast cancer and 80-90% of families with increased risk of early onset breast and ovarian cancer. Other examples of genes for which the population displays extensive allelic heterogeneity and which have been implicated in disease include CFTR (cystic fibrosis), dystrophin (Duchenne muscular dystrophy, and Becker muscular dystrophy), and p53 (Li-Fraumeni syndrome) among many others.

Accuracy in detection of mutations is extremely important, particularly in clinical settings. Methods for mutation detection can be divided into two groups: scanning methods that can detect previously unknown nucleotide differences, and methods designed to detect specific, known mutations or polymorphisms. Methods for the detection of known nucleotide differences currently include the following techniques: hybridization with allele-specific oligonucleotides (ASO); allele-specific PCR; solid-phase minisequencing; oligonucleotide ligation assay; allele-specific ligase chain reaction (LCR) among others. For the analysis of genomic DNA, these methods involve amplification of a specific DNA segment, followed by detection analysis to determine which allele is present. These methods are, however, ill suited for automated analysis of multiple mutations or multiple samples.

An automated method for detecting mutations, called "spectral genotyping," has been described previously, in which alleles are identified by fluorescent colors generated in sealed amplification tubes. In this technique, amplification is carried out in the presence of molecular beacons, which are probes that become fluorescent when they hybridize to their target. Tyagi et al. demonstrated that probes with a reporter at the 5' end and a quencher at the 3' end can be used to distinguish alleles. Tyagi S and Kramer F R (1996) Molecular beacons: probes that fluoresce upon hybridization. *Nat. Biotechnol.* 14, 303-308. Molecular beacons are hairpin-shaped, single-stranded oligonucleotides consisting of a probe sequence embedded within complementary sequences that form a hairpin stem. A fluorophore is covalently attached to one end of the oligonucleotide, and a non-fluorescent quencher is covalently attached to the other end. In the absence of a target, the fluorophore is held close to the quencher and fluorescence cannot occur. When the probe binds to its target, the rigidity of the probe-target helix forces the stem to unwind, resulting in the separation of the fluorophore and quencher, and restoration of fluorescence. These probes can detect a number of different targets in the same solution. This is accomplished by constructing a different molecular beacon for each target and attaching a differently colored fluorophore to each. The probes are placed in the same amplification tube, and the color that develops indicates which targets were present. For genotyping alleles, two molecular beacons are used, one specific for the wild-type allele and labeled with a green fluorophore and the other specific for the mutant allele and labeled with a red fluorophore. The appearance of green fluorescence during amplification indicates homozygous wild-types, red fluorescence indicates homozygous mutants, and both green and red fluorescence indicates heterozygotes.

This procedure was used in the past to distinguish, for example, alleles of the beta-chemokine receptor 5 (CCR5) gene that determines susceptibility to infection by the human immunodeficiency virus (HIV). Individuals homozygous for a 32-nucleotide deletion in this gene (CCR5D32) are largely resistant to HIV infection, despite multiple sexual contacts with HIV-infected individuals, and heterozygotes are partially protected against disease progression. To understand the susceptibility of human populations to the spread of HIV, large-scale epidemiological studies of the distribution of this mutant allele are needed, necessitating high-throughput assays. Therefore, an automated spectral genotyping assay was developed that identifies CCR5 alleles. For the detection of the wild-type allele, a fluorescein-labeled molecular beacon was prepared whose probe sequence was complementary to the region that is deleted in the mutant; for the detection of the mutant allele, a tetramethylrhodamine-labeled molecular beacon was synthesized that was complementary to the sequences flanking the region of the deletion, which are brought together in the mutant. Human DNA samples were used as templates for polymerase chain reactions (PCRS) in which the region of the CCR5 gene that encompasses the site of the D32 mutation was amplified in the presence of both molecular beacons. The sequence of the wild-type-specific molecular beacon was green fluorescent fluorescein-5'-CG-GTCTGGAAATTCTTCCAGAATTGATACTGACCGG-3'-DABCYL and the sequence of the mutant-specific molecular beacon was red fluorescent tetramethylrhodamine-5'-CGGC-TATCTTTAATGTATGGAAAATGAGAGCCG-3-DAB-CYL, and where DABCYL is the quencher 4-(4'-dimethylaminophenylazo) benzoic acid. Furthermore, the allele discrimination was demonstrated for two alleles in the human insulin gene that differ by only a single A-T nucleotide substitution.

It is apparent from the above that one is limited to only three reaction outcomes at one time. Thus, while assays for allele identification are now available, these assays can not measure more than a few distinct parameters or analytes simultaneously. This limitation stems from the technical difficulty of measuring several labels simultaneously.

This problem with conventional multiplex assays has been recently solved with Luminex proprietary LabMAP system which typically detects 100 analytes simultaneously in the same reagent mixture (see for detailed description of the technology at website www.luminexcorp.com). This significant advantage is largely attributable to the availability of fluorescently addressable microspheres, specially designed flow cytometry apparatus and related assay methods as described in detail in commonly owned U.S. Pat. Nos. 6,046, 807; 5,981,180; and 5,736,330. The present invention provides further and unexpected improvements to this multiplex method and allows the identification of more than 100 different analytes simultaneously, while using the same set of 100 fluorescently addressable microspheres.

SUMMARY OF THE INVENTION

In one embodiment, the instant invention relates to a method for the detection of a plurality of reactive sites on an analyte, the method comprising: (1) providing a population of microspheres, wherein each of the microspheres carries a plurality of fluorescently-labeled reactants capable of reacting respectively with the plurality of reactive sites; (2) allowing the reactants and the reactive sites to react, thereby forming reactant-reactive site pairs which are distinguishable by fluorescence intensity from each other; and (3) detecting the reactant-reactive site pairs formed, whereby the presence or absence of each of the plurality of reactive sites on the analyte is determining.

Preferable reactants for the instant invention are distinguishable from each other by their fluorescence intensity, and preferable methods for detecting the reactant-reactive site pairs include flow cytometry methods well known to those skilled in the art.

The method of the instant inventions is particularly suitable where the analyte is a nucleic acid molecule, the reactive site is one or more alleles of a locus on the nucleic acid molecule, and the reactant is one or more fluorescently-labeled nucleic acid probes respectively specific for the one or more alleles. Optionally, the nucleic acid molecule has been subject to in vitro manipulation, such as but not limited to PCR amplification, a restriction enzyme digestion, strand displacement amplification (SDA), transcription mediated amplification (TMA), ligase chain reaction (LCR), nucleic acid sequence based amplification (NASBA), primer extension, rolling circle amplification, primer extension, amplification of RNA by an RNA-directed RNA polymerase, or a combination thereof.

In another embodiment, the instant invention teaches a method for determining allele zygosity of nucleic acid molecules of a genetic locus having two alleles, the method comprising: (1) providing a population of microspheres, wherein each of the microspheres carries two fluorescently-labeled nucleic acid probes respectively specific to each of the two alleles; (2) allowing the probes to hybridize to the alleles, thereby forming allele-probe pairs which are distinguishable by fluorescence intensity; and (3) detecting the presence or absence and fluorescence intensity of the allele-probe pairs, whereby the allele zygosity of the locus is determined. Preferably, the probes are distinguishable from each other by their fluorescence intensity. Suitable methods for detecting the allele-probe pairs include flow cytometry methods well-known to those skilled in the art. Optionally, the nucleic acid molecules have been subject to in vitro manipulation, such as but not limited to PCR amplification, a restriction enzyme digestion, strand displacement amplification (SDA), transcription mediated amplification (TMA), ligase chain reaction (LCR), nucleic acid sequence based amplification (NASBA), primer extension, rolling circle amplification, primer extension, amplification of RNA by an RNA-directed RNA polymerase, or a combination thereof.

A further embodiment of the invention teaches a method for determining polymorphism of nucleic acid molecules of a genetic locus having multiple alleles, the method comprising: (1) providing a population of microspheres, wherein each of the microspheres carries multiple fluorescently-labeled nucleic acid probes respectively specific to each of the multiple alleles; (2) allowing the probes to hybridize to the alleles, thereby forming allele-probe pairs which are distinguishable by fluorescence intensity; and (3) detecting the presence or absence and fluorescence intensity of the allele-probe pairs, whereby the allele polymorphisms of the locus is determined. Suitable probes may be distinguishable from each other by their fluorescence intensity, and suitable methods for detecting the reactant-reactive site pairs include flow cytometry methods well known to those skilled in the art. In a preferable embodiment, the nucleic acid molecules have been subject to in vitro manipulation, such as PCR amplification, a restriction enzyme digestion, strand displacement amplification (SDA), transcription mediated amplification (TMA), ligase chain reaction (LCR), nucleic acid sequence based amplification (NASBA), primer extension, rolling circle amplification, primer extension, amplification of RNA by an RNA-directed RNA polymerase, or a combination thereof. The inventive method is particularly suitable to analyze nucleic acid molecules that comprise a mixture of nucleic acid molecules from more than one organism, such as from different individuals of the same species.

In still another embodiment, the instant invention provides a method for detecting a plurality of analytes in a sample, the method comprising (1) providing a population of microspheres, wherein each microsphere carries a reactant capable of reacting respectively to each of the plurality of analytes; (2) allowing the reactant and the analytes to react, thereby forming reactant-analyte pairs; (3) providing a mixture of a plurality of reporter reagents capable of reacting with the reactant-analyte pairs; (4) allowing the reporter reagents to react with the reactant-analyte pairs to form reactant-analyte-reporter reagent complexes which are distinguishable by fluorescence intensity; and (5) detecting the presence or absence of the reactant-analyte-reporter reagent complexes formed, whereby the presence or absence of each of the plurality of analytes is determined. Preferably, the reporter reagents specific for each reactant-analyte pair are distinguishable from each other by their fluorescence intensity. Flow cytometry methods well known to those of skill in the art are suitable for detecting the reactant-analyte-reporter reagent complexes are detected using. In a preferred embodiment, the analytes are immunoglobulins, the reactant is an antigen, such as insulin, that binds to the immunoglubulins, and the reporter agents are fluorescently-labeled anti-immunoglobulin antibodies. In another preferred embodiment, the antigen molecule is a human chorionic gonadotropin (hCG) related molecule, and the reactive site is a alpha-subunit or a variant thereof, or a beta-subunit or a variant thereof, and the reactant is a respective antibody.

In yet another preferred embodiment, the analytes are alleles of target nucleic acid molecules of a genetic locus, the reactant is a capture probe complementary to a common sequence within the locus, and the reporter agents are reporter probes specific to the individual alleles. Preferably, the alleles are fluorescently labeled. More preferably, the capture probe abuts its respective reporter probe on the target nucleic acid molecule, the reactant-analyte-reporter reagent complex is formed via oligonucleotide ligation assay, and the complex is analyzed via a flow cytometer, preferably the complex has been heated to denature the complex so as to remove the target nucleic acid molecule from the complex.

According to yet another embodiment of the invention, a method is provided for detecting a plurality of SNPs in nucleic acid molecules, each SNP having two or more polymorphisms, the method comprising: (1) providing a plurality of populations of microspheres, wherein each population corresponds to a SNP and has an addressable signature, and wherein each of the microspheres in a population carries two or more fluorescently-labeled nucleic acid probes specific respectively to each of the polymorphisms for the SNP; (2) allowing the probes to hybridize to the SNPs, thereby forming SNP-probe pairs which are distinguishable by fluorescence intensity; and (3) determining the presence or absence and type of SNP via detecting the presence or absence and fluorescence intensity of the SNP-probe pairs and the corresponding microsphere signature. Preferably, the probes on a microsphere are distinguishable from each other by their fluorescence intensity. Flow cytometry methods well known to those of skill in the art are suitable for detecting the SNP-probe pairs. Optionally, the nucleic acid molecules have been subject to in vitro manipulation, such as PCR amplification, a restriction enzyme digestion, strand displacement amplification (SDA), transcription mediated amplification (TMA), ligase chain reaction (LCR), nucleic acid sequence based amplification (NASBA), primer extension, rolling circle amplification, primer extension, amplification of RNA by an RNA-directed RNA polymerase, or a combination thereof. Optionally, to decrease accuracy and to increase detection limit, the nucleic acid molecules are fragmented such that the SNP-probe pairs are suitable for flow cytometry analysis.

The instant invention also provides for a composition comprising an addressable microsphere, the microsphere carrying a mixture of at least two fluorescent reactants capable of forming reactant-analyte pairs with a respective analyte in a sample, and the reactant-analyte pairs are detectably distinguishable from each other by their fluorescence intensity. Preferably the reactants are detectably distinguishable from each other by their fluorescence intensity. Further provided is a kit for the detection of a plurality of analytes in a sample, the kit comprising (1) a composition comprising a population of microspheres, wherein each microsphere carries a reactant capable of reacting respectively with the plurality of analytes to form reactant-analyte pairs; and (2) a mixture of a plurality of reporter reagents corresponding to the plurality of analytes, wherein the reporter reagents are capable of reacting with the reactant-analyte pairs to reactant-analyte-reporter reagent complexes which distinguishable from each other by fluorescence intensity. Preferably, the reporter reagents are distinguishable from each other by their fluorescence intensity. In a particular embodiment, the analytes are immunoglobulins, the reactant is an antigen, such as insulin, that binds to the immunoglubulins, and the reporter agents are fluorescently-labeled anti-immunoglobulin antibodies.

DETAILED DESCRIPTION OF THE INVENTION

Figure 1:
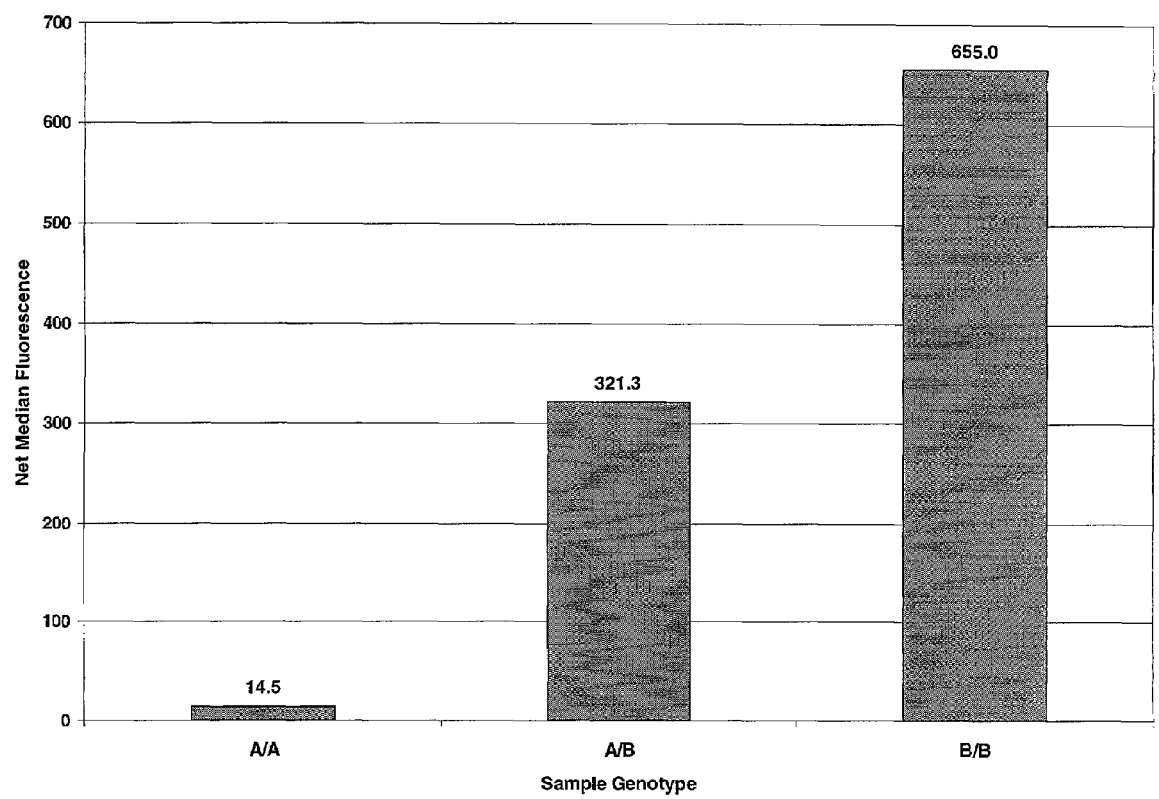
FIG. 1 illustrates that in a dual reporter read-out assay using direct hybridization, the fluorescence intensity of heterozygous (A/B) allele is half-way between the respective fluorescence intensities of homozygous (A/A and B/B) alleles.

This invention provides an improved method of detecting a higher number of analytes than was previously possible with fluorescently addressable microspheres.

The term "analyte" is generally understood as a molecular species such as a nucleic acid or protein sought to be detected, quantitated and/or identified.

The instant methods and compositions expand drastically the number of analytes to be analyzed but rely on the same number of currently available fluorescently addressable microspheres. This novel approach adds a new dimension and breadth to existing detection methods.

Various applications of this method are contemplated. Specifically, one preferred variation is directed at detection of a nucleic acid molecule (or a polynucleotide molecule, such as a DNA or an RNA molecule), or its variants, by monitoring the formation or dissociation of a complex consisting of: a target nucleic acid sequence (analyte) containing the locus (reactive site) of a variation; an oligonucleotide or DNA analogue probe (reactant) specific for one allele of the variation and capable of hybridizing and forming a probe-analyte complex; a reporter molecule, e.g., fluorophore, signaling the formation of a hybrid. In addition means of recording are disclosed at which a change in reaction output signal occurs which is attributable to formation or dissociation of the complex and is thereby correlated with the strength with which the probe hybridized to the target sequence. Fluorescent markers or fluorophores are convenient as markers to underline variations in fluorescence intensity or emission spectra (color) resulting from denaturization or hybridization of the complex.

The present invention overcomes prior art problems by employing so-called fluorescently addressable microspheres. These microspheres typically incorporate one, two or more dyes at different dye-to-dye ratios so that fluorescence reading machines like flow cytometers or fluorometers can index the particles according to their unique fluorescence "signature." Thus, each individual solid phase particle can be assigned a unique index number "encoded" to a particular set of particles, that can be retrieved at any time, e.g., at one time during the assay, at multiple times during the assay, or continuously during the assay. The index number or signature also contains information about the characteristics of the reactant, e.g. the nucleotide sequence of the oligonucleotide probe deposited on the surface of the particle, the catalog number of a DNA fragment deposited on the particle, index numbers of chemical steps which were involved in the chemical synthesis of an oligonucleotide bound to the particle, or some other relevant characteristics of the deposited molecules as required, e.g., antibody or antigen specificity and/or affinity.

In a specific example of multiplex assay of this invention, one or more classes of multifluorescent particles, each carrying a unique signature and constructed to bind one or more different nucleic acid sequence, are incubated with the sample in a single vessel. After necessary washes or preferably without any washing steps, incubations and additions are performed, the solid phase, i.e., microsphere or microparticle, is analyzed to detect a label indicative of binding of nucleic acid in the sample to the reactant oligonucleotide probe, such as fluorescence, luminescence, color, radioactivity or the like. Solid phase analysis is either preceded or followed by decoding of the index numbers programmed on the microspheres. Determination of the label and "decoding" the identity of the sample can be done manually although an automated instrument that would perform fluorescence reading function is more preferable.

As a generic embodiment of the invention, a method for determining the presence or absence of an analyte and variants thereof, e.g., alleles, mutants, isomers, epitopes, etc., in a sample is sought which comprises the steps of providing at least one set of fluorescently addressable microspheres, said set carrying a mixture of reactants for a respective analyte and variants thereof. The set generally carries a substantially equal mixture of the reactants for each of said analytes.

For example, two discreet reactants (A and B) are present on the bead surface at one time, which would allow the detection of three possible analyte variants or reactive sites (A, B, and AB, or AA, BB, and AB) in the sample. A reaction is then performed to form a pair between the variant-specific reactive site on the analyte and the respective reactant.

Optionally, and when necessary or desirable, one or more secondary reagents, or reporter reagents, are provided, such that the analyte/reactive-site pair can be rendered detectable by the measurement instrument. Preferably, two or more secondary reagents are provided, each of which is specific to the respective analyte-reactant pairs. Accordingly the presence or absence of the analyte and variants thereof is then determined based on fluorescence signature of carrier microsphere and the detectable characteristic of the analyte/reactant pair (e.g. a fluorescence signal, or a color) from the secondary reagents or reporter reagents.

In one aspect, the present invention provides a method for detecting nucleic acids and variants thereof as analytes in the sample. In another aspect, the present invention provides a method for detecting proteins and variants thereof as being analytes in the sample. In both aspects solid phase particles having distinguishable fluorescent signatures are preferably used.

One of the preferred embodiments of the invention involves a method for determining an allele zygosity of a nucleic acid in a sample. A set of microspheres are first prepared, each microsphere carries an equal mixture of the two nucleic acid probes for each of two alleles, A and B. These two probes are distinguishably labeled. Allele-probe hybridization is then performed, forming allele/probe pairs. Finally, signal strength for each allele/probe pair is measured, and allele zygosity is then determined according to the signal strength. If the zygosity is AA, then only probe A's signal is detected. If the zygosity is BB, only B probe signal is detected. If the zygosity is AB, then an equal strength of A and B probe signals are detected. An example of such a method is depicted in FIG. 1.

What is important and innovative, is that a single set of microspheres carrying a substantially equal mixture of the nucleic acid probes for each of said alleles can provide substantially the same information that previously required two or even three sets of microspheres, one for each of homozygous alleles and one for a heterozygous allele.

While the preferred mixture of probes bound to a microsphere is at one-to-one ratio it is clear that other mixing ratios are equally suitable as needed for a particular assay condition. In addition to 1:1 ratio these ratios can be in any conformation such as for example 1:2; 1:3; 1:10; 1:25; 1:100 and alike.

According to this method either the probe or the nucleic acid, i.e., analyte, in the sample are labeled with the fluorescent reporter, and each reporter is specific for each chosen allele. Further, the measuring step of the fluorescence signal comprises measuring either fluorescence intensity or fluorescence color or other well known means of light differentiation.

It is preferable that the microspheres carrying the probe are fluorescently addressable microspheres.

Optionally, the nucleic acid can be amplified by standard amplification means such as polymerase chain reaction (PCR), strand displacement amplification (SDA), transcription mediated amplification (TMA), ligase chain reaction (LCR), nucleic acid sequence based amplification (NASBA), self-sustained sequence based amplification (3SR), rolling circle amplification, amplification of RNA by an RNA-directed RNA polymerase and the like.

The alleles suitable as analytes of interest can be any one selected from the collection of Archaean, Bacterial, Eukaryotic, Viral, Viroid genes and ESTs found for example in GENBANK or any other periodically updated databases available commercially or free of charge. The preferred method accordingly contemplates DNA, RNA, exon or intron sequence, a part of an exon sequence and a part of an intron sequence, a genomic sequence, a gene of an infectious agent like bacteria, viruses, rickettsia, fungi, mycoplasma, chlamydia, or protozoa. Preferably, but not necessary, the genetic sequence of the nucleic acid belongs to a polymorphic gene.

As another embodiment, the non-nucleic acid analytes are contemplated as including but not limited to proteins. Some proteins in addition to amino acids may contain a nonprotein moiety, called prosthetic group, which is attached by covalent, heteropolar, or co-ordinate linkage. Proteins containing prosthetic groups such as carbohydrates, lipids, nucleic acids, metals, chromogens, heme groups and phosphate residues are accordingly called as glycoproteins, proteoglycans, lipoproteins, nucleoproteins, metalloproteins, chromoproteins, hemoproteins, and phosphoproteins.

The analytes of interest may also include not only prosthetic proteins but also natural and synthetic peptides, amino acid derivatives, blocked amino acids, as well as amine containing molecules such as cyanidins, biogenic amines such as ethanolamines, polymethylene diamines, polyamines, imidazolylalkylamines, phenylalkylamines, catecholamines, indolylalkylamines, betaines, or any other natural or synthetic derivatives of amino acids. These may further include diacids, hydrazines, aliphatic or aromatic amines. Among classes of biogenic amines there are many biologically important substances, e.g., choline, acetylcholine, muscarine, putrescine, cadaverine, spermine, histamine, mescaline, tyramine, hordenine, adrenaline, noradrenaline, dopamine, tryptamine, serotonin, carnitive, etc. Also contemplated are pharmacological analytes, e.g., drugs, prodrugs, and metabolites thereof. These compounds can be labeled with light-emitting dyes, either directly or through secondary reagents as for example in an immunoassay setting. Alternatively, they do not have to be labeled with an extra dye as some can autofluoresce, e.g., histamine or coumarin.

In a most preferred embodiment, the inventive methods and compositions can be used to detect single nucleotide polymorphism (SNP) in an organism. Specifically, a set of addressable microspheres can be labeled with polynucleotide probes specific for one SNP site, and another set can be labeled with probes for another SNP site. Because usually an organism contains multiple SNP sites, multiple addressable microspheres are labeled for each of the SNP sites. A mixture of these multiple, addressable, yet uniquely labeled microspheres can be used to detect the multiple SNP sites simultaneously. This approach overcomes the need to label the various polynucleotide probes distinctly, so long as the polynucleotide probes on a single microsphere is detectably distinguishable.

By "detectably distinguishable," it is meant that the reactant, for example, a polynucleotide probe, either before or after it has reacted with its respective reactive site of the analyte, can be distinguished by an instrument that classifies the individual microparticle, from all other reactant on the same microparticle. For example, if a microparticle carries two or more allele-specific probes for a SNP site, these two or more probes are labeled distinctly such that they are distinguishable by the instrument, e.g., a flowcytometer. As a particuarly preferred example, these probes are labeled with different fluorescent labels with different fluorescent spectra. A skilled artisan will readily recognize, however, the same fluorescent labels may be used on another microsphere with a different signature.

According to a preferred embodiment of the invention, multiple SNP sites may be detected simultaneously, by using multiple, addressable microspheres, even though the polynucleotide probe for each SNP site is labeled with the same characteristics, e.g. a radioactive isotope or a fluorescent marker, so long as the microspheres carrying the probes are distinguishable and can be identified and classified by the instrument with regard to the SNP site for which the microsphere is specific.

The methods and composition of the instant invention may also be applied in the field of variation detection among non-nucleic acid molecules, e.g., proteins and variants thereof, drugs and metabolites thereof, pathogens and mutants thereof, environmental pollutants and variants thereof, forensic specimens and variants thereof, and a variety of other applications including but not limited to industrial processing, medical surgery and treatment, meteorology, military applications, micromachining, nanotechnology, optical storage, labeling, spectroscopy research and many other related applications. The principle of the analysis, however, is the same, instead of hybridization one uses a reaction that relies on specificity of protein-protein interaction like in antibody-antigen interaction in a manner very similar to hybridization interaction (pair formation). Other specific molecule interactions are easily imaginable including but not limited to DNA-protein interaction, drug-DNA interaction, PNA-DNA interaction, etc. Other chemical pair-forming reactions can be advantageously used as well including covalent bonds, hydrogen bonds, van der Vaals interactions, etc. As can be appreciated by those skilled in the art, a large number of analytes can be detected using the present methods. In theory any target analyte for which a binding ligand or reactant, described below, can be detected using the methods of the invention.

Particularly, the application which can be readily imagined is application in various immunoassays usually involving antibody or antigen immobilized on solid phase (bead surface), including immunodiagnostic and agglutination tests. Listed below are representative examples wherein such potential exists: In human clinical and therapeutic application one needs to determine simultaneously several analytes and variants thereof, e.g., interrelated analytes (prodrug, drug and drug metabolites) or unrelated (various unrelated drugs given or taken by the same patient). These can include antibiotics/antimicrobial drugs such as gentamicin, tobramycin, amikacin, penicillin, cephalosporin, blasticidin S, viomycin, sulfa drugs, kanamycin, netilmicin, streptomycin, and vancomycin. Drugs of abuse such as opiates, barbiturates, amphetamines, methadone, cocaine, benzodiazepines, propoxyphene, phencyclidine (PCP), cannabinoids (THC), or lysergic acid diethylamide (LSD). Antiepileptic drugs such as phenytoin, phenobarbital, carbamazepine, primidone, ethosuximide, or valproic acid. Antiasthmatic drugs such as theophylline. Cardioactive drugs such as digoxin, digitoxin, lidocaine, procainamide, N-acetylprocainamide, quinidine, propranolol, diisopyramide, or flecainide. Chemotherapeutic drugs such as methotrexate. Hormones such as testosterone, estradiol, estrogens, progesterone, cortisol, thyroxine, insulin, human placental lactogen (HPL), thyroid-stimulating hormone (TSH), follicle-stimulating hormone (FSH), luteinizing hormone (LH), or human chorionic gonadotropin (hCG). Immunosuppressants such as cyclosporin A (CsA), cyclosporin G (CsG, OG37-325), or FK5O6 (tacrolimus). Serum proteins such as albumin, alpha-1-acid glycoprotein (orosomucoid), serum amyloid P component (SAP), serum retinol binding protein, thyroxine binding globulin (TBG), alpha-1-antitrypsin, beta2-macroglobulin, anti-DNA antibodies, antithrombin III, apolipoproteins AI and AII, apolipoprotein BI, prealbumin (transthyretin), C1 inactivator, C3 protein, ceruloplasmin, fibronectin, haptoglobin, hemopexin, somatotropin, transferrin, immune complexes, immunoglobulin A, immunoglobulin E, immunoglobulin G and its subclasses, immunoglobulin M, immunoglobulin light chains, rheumatoid factor, alphal-microglobulin, C1-esterase inhibitor, C4-protein, or C-reactive protein. Various tumor markers, e.g., alpha-Fetoprotein, carcinoembryonic antigen (CEA), human chorionic gonadotropin (hCG), beta-hCG, pregnancy-specific protein (SP1), placenta-specific protein (PPS), placental alkaline phosphatase (Regan type), isoferritins, tissue polypeptide antigen, Tennessee antigen, pancreatic oncofetal antigen (POA), prostatic acid phosphatase, carbohydrate antigen 19-9 (sialyl Lewis), carbohydrate antigen 50, cancer antigen 125, cancer antigen 15-3, fecal occult blood, alpha2-macroglobulin, neuron specific enolase, or squamous cell carcinoma antigen. Many allergens such as total serum IgE, allergen-specific IgEs, pollen allergens, epithelial allergens, house dust, occupational dusts, molds, foods, chemicals, or drugs. Similar applications can be imagined in parasitic and infectious diseases and/or causal organisms—human immunodeficiency virus (HIV), hepatitis, influenza, herpes, toxoplasma, rubella, cytomegalovirus (CMV), adenovirus, coxsackieviruses, arbovirus, malaria, schistosomiasis, trypanosomes, trichinella, chlamydia trachomatis, neisseria gonorrhoeae, amoebiasis, typhoid, leprosy, or tuberculosis.

For example, to determine an HIV infection in a suspect patient, a Western Blot assay is often used to assure the presence of antibodies against major antigenic determinants of the virus. Having an antibody against only one immunogenic component of HIV will usually be considered as false positive reaction to an unrelated antigen shared with viral antigen. Thus one needs to have multiplexed assay which will provide result in regard to several antigens simultaneously.

Other applications for this invention include for example autoimmune diseases, e.g., rheumatoid factor (RF), polyarthritis, juvenile chronic polyarthritis, ankylozing spondylitis, Reiter's syndrome, antinuclear antibodies (ANA), anti-DNA antibodies, antihistone antibodies, acetylcholine receptor antibodies, antierythrocyte antibodies, antiplatelet antibodies, or thyroglobulin antibodies. In quantitating bacterial, mycoplasmal, and fungal antigens and antibodies like *Salmonella* O antigens, *Vibrio cholerae* O antigens and exotoxins, *Escherichia coli* O and K antigens, *Haemophilus influenzae* polysaccharide, *Treponema pallidum, Brucella* and *Yersinia enterocolitica* O antigens, *Francisella rularensis* O antigen, *Candida albicans* and *Aspergillus fumigalus* cell wall and cytoplasmic antigens, *Streptococcus* M protein, *Mycoplasma, Rickettsia, Chlamy-* dia, *Clostridium* tetanus exotoxin, or Corynebacterium diphtheria exotoxin. Equally important application can be found in agricultural field. For example, in measuring plant hormones like cytokinins, gibberellins, indole-3-acetic acid, or abscisic acid. In detecting spoilage microorganisms—*Erwinia* spp., *Fusarium* spp., *Humicola lanuginosa, Legionella pneumophila, Ophiostoma ulmi, Phylophthora megasperma, Pseudocercosporella herpotrichoids. Pseudomonas syringae, Rhizoctonia solani, Xanthomonas campestris.* In identifying plant viral agents—Beet necrotic yellow vein virus, cauliflower mosaic virus, citrus tristeza virus, cucumber mosaic virus, elongated potato virus, isometric plant viruses, pea seed-borne mosaic virus, potyviruses, soybean mosaic viruses, or zucchini yellow mosaic virus. One can find widespread application in the food industry by measuring for example bacterial toxins—*Clostridium botulinum* neurotoxins A, B, E, F, and G; *Staphylococcus aureus,* or enterotoxins A, B, C, D, and E. Food safety concerns can be equally addressed by detecting mycotoxins, aflatoxins B1, BC, B1diol, M1 and Q1, ochratoxin, T-2 toxin, 31-OH-T-2 toxin, T-2 tetraoltetraacetate, HT-2 toxin, group A trichothecencs, rotidin A, zearalenone, rubratoxin B, sterigmatocystin, deoxyverrucarol, or deoxynivalenol. Also in the category of food safety one can analyze pathogenic microorganisms such as *Salmonella, Listeria monocytogenes, Escherichia coli, Vibrio* spp., *Yersinia enterocolitica,* or *Campylobacter jejuni* and mutants thereof. Miscellaneous health issues such as mushroom poisoning, algal and seafood toxins, or potato glycoalkaloids can be addressed. Various food enzymes such as alpha-mylase, alpha-amylase, catalase inhibitor, chymotrypsin, debranching enzyme, lipase, malate dehydrogenase, papain, pepsin, polyphenoloxidase, proteolytic enzymes, and trypsin can be successfully measured. In addition, interspecies meat and adulterant identification can be deployed using the invention, e.g., beef, sheep, pig, goat, horse, meat products, sausages, processed meats. Food additives such as biocides, water treatment chemicals, plastic additives, and petroleum product additives can be also detected as well. Similarly, this invention can find application in veterinary practice; e.g., in livestock diseases and/or causal organisms—*Toxoplasma gondii, Brucella abortus, Stephanauras dentatus, Mycoplasma bovis, Leptospira interrogans, Trichinella spiralis, Mycobacterium paratuberculosis,* bovine rhinotracheitis, maedi-visna virus, swine fever virus, coronavirus, Aujeszky's disease, swine vesicular disease, enzootic bovine leukemia, foot and mouth disease, avian PMV1, rotavirus, or sheep lungworm disease. Other veterinary uses can be imagined such as detection of anabolic agents, i.e.,17beta-Estradiol, estrone, testosterone, 17-methyltestosterone, progesterone, trenbolone, diethylstilbestrol, hexoestrol, zeronal, or therapeutic agents, i.e., cephalexin, chloramphenicol, colistin, gentamicin, hydromycin B, monensin, sulfonamides, penicillins, or cephalosporins.

Without limiting to the above examples one can easily adapt the invention to measure immobilized reactants for environmental testing applications aimed at identifying and measuring pesticides and their aminated metabolites including but not limited to aldrin, alachlor, atrazine, BAY SIR 8514, S-bioallethrin, chlorosulfuron, cyanazine, 2,4-D, DDT, dichlorfop-methyl, dieldrin, diflubenzuron, endosulfon, iprodione, kepone, maleic hydrazide, metalaxyl, oxfendazole, parathion, paraoxon, paraquat, pentachlorophenol, 2,4, 5-T, terbutryn, triadimefon, warfarin. Environmental pollutants of concern, e.g., polychlorinated biphenyls (PCBs), polybrominated biphenyls (PBBs), polynuclear aromatic hydrocarbons (PARs), nitroaromatics, cyclic ketones, BTEX (benzene, toluene, ethyl benzene, and xylene), nitrosamines, haloalkanes, dioxins, dibenzofurans, or TNT can be imagined as being quantifiable by the instant method.

Other uses can include the field of combinatorial chemistry, e.g., screening of combinatorial libraries that could include any receptor-ligand, protein subunit interactions, drugs, nucleic acid binding assays, or enzymatic assays. Applicability of the process can be imagined in receptor-ligand assays, i.e., receptor or ligand immobilized on solid phase, e.g. characterization of receptor-ligand interactions such as hormone binding events; in protein subunit interactions—protein subunit immobilized on solid phase, e.g., characterization of protein subunit associations; in nucleic acid binding assays, e.g., antibody to specific nucleic acid sequence or nucleic acid binding protein immobilized on solid phase, e.g., transcriptional factor binding; in enzymatic assays—enzyme or proteinaceous subunit on solid phase, e.g., activation or inactivation of proenzymes such as complement or clotting factors; in pre-coated (activated) particles—amine-containing capturing component immobilized on solid phase for easy immobilization of other reactants, e.g., protein G, protein A, avidin, streptavidin, neutravidin; and also in affinity purification columns—proteinaceous capturing component immobilized on solid phase (usually beads) for immobilization of target molecules, e.g., protein G, antigen-antibody. Thus, a variety of applications for the process can be imagined and as disclosed herein these examples are not in any way limiting but serve only for the purpose to illustrate these and many other possible applications requiring quantitative data.

The current Luminex LabMAP system utilizes fluorescently addressable microspheres as the substrate surface for biomolecular reactions, the products of which are in turn detected by separate fluorescent reporters. Currently, two fluorescent internal dyes are used to provide 100 distinct microsphere sets incorporating them and a third dye is used as a reporter fluorochrome to indicate the extent of the biological/chemical reaction. With 100 separately addressable members of this suspension array, 100 separate analytes can be assayed simultaneously. The present invention expands the number of analyzable analytes up to three hundred separate analytes. With the current LabMAP system only 50 SNP sites (two alleles per site, e.g., wild-type and mutant homozygotes) can be interrogated simultaneously by using 100 sets of fluorescently addressable beads. The present inventors discovered that utilizing the same sets of microspheres as in homozygote detection one simultaneously detect heterozygote forms of these alleles. As a result the capacity of Luminex LabMAP multiplexed assays is increased by at least three fold to 300 simultaneous measurements.

Various embodiments of this discovery are imaginable. As an example, genetic variation is commonly distributed as biallelic variation, i.e., two allelic forms of the particular site. Single nucleotide polymorphism (SNP) is commonly of this type, with two forms distributing in typical Mendelian fashion. Because SNPs are distributed throughout the genome they are considered useful markers in the molecular and genetic linkage studies of interest in pharmacogenomics and other medical and biological fields.

A protocol for synthesizing molecular beacons is available at www.phri.nyu.edu/molecular_beacons. Molecular beacons are oligonucleotide probes that can report the presence of specific nucleic acids in homogeneous solutions. They are useful in situations where it is either not possible or desirable to isolate the probe-target hybrids from an excess of the hybridization probes, such as in real-time monitoring of polymerase chain reactions in sealed tubes or in detection of RNAs within living cells. Molecular beacons are hairpin-shaped molecules with an internally quenched fluorophore whose fluorescence is restored when they bind to a target nucleic acid. They are designed in such a way that the loop portion of the molecule is a probe sequence complementary to a target nucleic acid molecule. The stem is formed by the annealing of complementary arm sequences on the ends of the probe sequence. A fluorescent moiety is attached to the end of one arm and a quenching moiety is attached to the end of the other arm. The stem keeps these two moieties in close proximity to each other, causing the fluorescence of the fluorophore to be quenched by energy transfer. Since the quencher moiety is a non-fluorescent chromophore and emits the energy that it receives from the fluorophore as heat, the probe is unable to fluoresce. When the probe encounters a target molecule, it forms a hybrid that is longer and more stable than the stem and its rigidity and length preclude the simultaneous existence of the stem hybrid.

Thus, the molecular beacon undergoes a spontaneous conformational reorganization that forces the stem apart, and causes the fluorophore and the quencher to move away from each other, leading to the restoration of fluorescence which can be detected.

Another approach can be based on using the 5' nuclease assay for allelic discrimination which is observed upon inefficient cleavage of a mismatched fluorogenic probe. This inefficient cleavage is observed even when there is only a single mismatch with a probe that is 20-30 nucleotides long.

DNA/protein interaction studies with molecular beacons are also feasible in a same manner as nucleic acid assays.

SNP scoring can be equally conducted using SNP-IT™ (SNP-Identification Technology™), primer-extension SNP scoring technology (Orchid Biosciences Inc., Princeton, N.J.). SNP Identification Technology primer extension is a method of isolating the precise location of the site of a suspected SNP and utilizing the inherent accuracy of DNA polymerase to determine the SNP's presence or absence. In SNP-IT primer extension, a specially synthesized DNA primer is bound to the sample DNA to expose the DNA site of interest where a SNP may be present. DNA polymerase, a naturally occurring molecule whose design is specifically tailored to accurately and reliably insert the appropriate complementary base to a chain of DNA, is then added to extend the DNA chain by one base at the suspected SNP location. This single base extension is then detected by one of several conventional methods, including fluorescence, optical density, electrophoresis and mass spectroscopy. The result is a direct read-out method of detecting SNPs that creates a simple binary "bit" of genetic information representing the presence of a SNP in a DNA sample (see for details at http://www.orchid.com).

Another means of conducting multiplex analysis can be adopted by using ligase/polymerase-mediated genetic bit analysis of single nucleotide polymorphisms and its use in genetic analysis. See for example U.S. Pat. No. 5,952,174 to Nikiforov, et. al. Accordingly a method is provided for determining the identity of a nucleotide at a preselected site in a nucleic acid molecule. The method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

Specifically, "Oligonucleotide Ligation Assay" (OLA) may be employed. OLA is a solid phase method that uses two oligonucleotides which are designed to be capable of hybridizing to abutting sequences of a single strand of a target. One of the oligonucleotides is preferably biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. OLA is capable of detecting point mutations. Nickerson, D. A. et al.have described a nucleic acid detection assay that combines attributes of PCR and OLA (Nickerson, D. A. et al., Proc. Natl. Acad. Sci. (U.S.A.) 87:8923-8927 (1990). In this method, PCR is used to achieve the exponential amplification of target DNA, which is then detected using OLA. Assays, such as the OLA, require that each candidate dNTP of a polymorphism be separately examined, using a separate set of oligonucleotides for each dNTP.

"Allele specific hybridization" as used herein refers to an assay to detect the presence or absence of a pre-determined sequence variation such as SNP in a sample containing homozygous or heterozygous polynucleotide or oligonucleotide of interest by hybridizing the polynucleotide or oligonucleotide of interest with a nucleic acid probe, e.g., DNA capture probe bound to a microsphere, of pre-determined sequence such that differential hybridization between homozygous or heterozygous nucleotide sequences in the sample is revealed by disparity in fluorescence intensity of hybridization products. For example, homozygotes will display either very bright or very dim fluorescent signal and heterozygotes will display intermediate intensity fluorescent signal. Alternatively, homozygotes will display fluorescent signals of distinct color, e.g., red and blue, and heterozygotes will display a fluorescent color resulting from mixture of these colors, e.g., green.

The alleles suitable as analytes of interest can be selected from the collection of Archaean, Bacterial, Eukaryotic, Viral, Viroid genes and nucleic acid sequences found for example in GENBANK or any other databases as well as updates thereof which are available commercially or free of charge. One skilled in the art can easily select such analytes and variants thereof from the Internet sites such as http://www.ncbi.nlm.nih.gov; http://www.celera.com/celerascience and alike.

Fluorescent dyes used in this invention are known in the art and may have emission wavelengths between 200 nm and 1,000 nm. However, any dye that is soluble in an organic solvent can be used. The squaric acid based fluorescent dyes can be synthesized by methods described in the literature. See, for example, Sprenger et al. Angew. Chem., 79, 581 (1967); Angew. Chem., 80, 541 (1968); and Maaks et al., Angew Chem. Intern. Edit., 5, 888 (1966). Additionally, unsymmetrically substituted squaric acid compounds can be synthesized by methods such as those described by Law et al., J. Org. Chem. 57, 3278, (1992). Specific methods of making some of such dyes are well known in the art and can be found for example in U.S. Pat. Nos. 5,795,981; 5,656,750; 5,492, 795; 4,677,045; 5,237,498; and 5,354,873. The practical use of above described fluorescent dyes, e.g., phthalocyanines, 2,3-naphthalocyanines, squaraines and croconic acid derivatives is disclosed in U.S. Pat. No. 5,525,516 issued to Krutak, et al. These dyes may contain methine groups and their number influences the spectral properties of the dye. The monomethine dyes that are pyridines typically have blue to blue-green fluorescence emission, while quinolines have green to yellow-green fluorescence emission. The trimethine dye analogs are substantially shifted toward red wavelengths, and the pentamethine dyes are shifted even further, often exhibiting infrared fluorescence emission (see for example U.S. Pat. No. 5,760,201).

Related dyes can be further selected from cyclobutenedione derivatives, substituted cephalosporin compounds, fluorinated squaraine compositions, symmetrical and unsymmetrical squaraines, alkylalkoxy squaraines, or squarylium compounds. Some of these dyes can fluoresce at near infrared as well as at infrared wavelengths that would effectively expand the range of emission spectra up to about 1,000 nm. In addition to squaraines, i.e., derived from squaric acid, hydrophobic dyes such as phthalocyanines and naphthalocyanines can be also selected as operating at longer wavelengths. Other classes of fluorochromes are equally suitable for use as dyes according to the present invention. Non-limiting examples of some of these dyes are listed herein: 3-Hydroxypyrene 5,8, 10-Tri Sulfonic acid, 5-Hydroxy Tryptamine, 5-Hydroxy Tryptamine (5-HT), Acid Fuhsin, Acridine Orange, Acridine Red, Acridine Yellow, Acriflavin, AFA (Acriflavin Feulgen SITSA), Alizarin Complexon, Alizarin Red, Allophycocyanin, ACMA, 4-dicycano-methylene-2-methyl-6-(p-dimethylaminostyrl)4H-pyran, fluorescent chelates of lanthanide ions, for example ions of Terbium, Samarium, and Europium, Aminoactinomycin D, Aminocoumarin, Anthroyl Stearate, Aryl- or Heteroaryl-substituted Polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy F1, BOPRO 1,Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH-CH3, DAPI, Diamino Phenyl Oxydiazole (DAO), Dimethylamino-5-Sulphonic acid, Dipyrrometheneboron Difluoride, Diphenyl Brilliant Flavine 7GFF, Dopamine, Eosin, Erythrosin ITC, Ethidium Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Hoechst 33258, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin E8G, Oregon Green, Oxazine, Oxazole, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin (PE) R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Texas Red, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO 1, or combinations thereof.

One skilled in the art would certainly know which one to select among such dyes as long as desired emission and absorption properties as well as their hydrophobic or hydrophilic properties are appropriate.

One skilled in the art would certainly know to select instead of above listed dyes so-called man-made "quantum dots" or "semiconductor nanocrystals", which usually consist of sulfide (S) or selenium (Se) of various metals such as Zn, Cd, Pb, Sn, Hg, Al, Ga, In, Ti, Si, Ag, Fe, Ni or Ca. Means of making quantum dots are well known in the art as disclosed for example in U.S. Pat. Nos. 5,906,670; 5,888,885; 5,229,320; and 5,482,890, which are incorporated herein by way of reference. Other metals are known which can fluoresce when in a chelated form (e.g., EDTA) and may include but are not limited to metals such as Tc, In, Ga, Sc, Fe, Co, Pr, Nd, Sm, Eu, Gd, Th, Dy, Ho, Er, Tm and Yb (e.g., U.S. Pat. No. 4,454,106 and 4,374,120).

Furthermore, naturally occuring minerals and crystals such as Clinohedrite, Hardystonite, Willemite, Witherite, Yellow Calcite, Tan Calcite, Terlingua Calcite, Amber, Scapolite, and Eucryptite among others, are also known to fluoresce when exposed to a short-wave high-energy excitation light (detailed list of some of such minerals can be found in U.S. Pat. Nos. 4,365,153; 4,336,459; and 4,236,071, which references are incorporated herein by way of reference). Specifically, minerals that are known to fluoresce in a blue spectrum include but are not limited to Benitoite, Hydrozincite, and Scheelite; those that emit green fluorescence include Chalcedony Rose, Hyalite Opal, Youngite, those that emit red fluorescence include Eucryptite, those that emit orange fluorescence include Halite, Svabite-Tilisite. There are also some minerals, which may, for example, emit fluorescent light in two separate light spectra such as Phlogopite/Diopside (yellow/blue colors respectively). Such minerals are used as such in crystalline form or can be ground into fine powders.

Preferably, fluorescent materials of the invention are present in the form of spherical microparticles or crystals or nanocrystals such as quantum dots. Physical shapes other than spherical particles, crystals, and powders can be incorporated within a shell barrier. One skilled in the art may utilize fluorescent fibers such as disclosed, for example, in U.S. Pat. No. 4,921,280, as incorporated herein by way of reference. Encapsulated fluorescent materials of the invention may also include light-excitable materials such as used in liquid crystal display (LCD) devices, which are disclosed in U.S. Pat. Nos. 3,998,526; 4,337,999; 4,425,029; 4,668,049; 5,039,206; and 5,052,784, as incorporated herein by way of reference.

The spectral properties of the fluorescent materials should be sufficiently similar in excitation wavelengths and intensity to commonly used fluorescent dyes like fluorescein or rhodamine derivatives as to permit the use of the same flow cytometry equipment and standard operation procedures practiced by those of ordinary skill. More preferably the dyes have the same or overlapping excitation spectra, but possess distinguishable emission spectra. Any detection system can be used to detect the difference in spectral characteristics between the two dyes, including a solid state detector, photomultiplier tube, photographic film, or eye, any of which may be used in conjunction with additional instrumentation such as a spectrometer, luminometer microscope, plate reader, fluorescent scanner, flow cytometer, or any combination thereof, to complete the detection system. Preferably dyes are chosen such that they possess substantially different emission spectra, preferably having emission maxima separated by greater than 10 nm, more preferably having emission maxima separated by greater than 25 nm, even more preferably separated by greater than 50 nm. When differentiation between the two dyes is accomplished by visual inspection, the two dyes preferably have emission wavelengths of perceptibly different colors to enhance visual discrimination. When it is desirable to differentiate between the two dyes using instrumental methods, a variety of filters and diffraction gratings allow the respective emission maxima to be independently detected. When two dyes are selected that possess similar emission maxima, instrumental discrimination can be enhanced by insuring that both dyes' emission spectra have similar integrated amplitudes, similar bandwidths, and the instrumental system's optical throughput be equivalent across the emission range of the two dyes. Instrumental discrimination can also be enhanced by selecting dyes with narrow bandwidths rather than broad bandwidths, however such dyes must necessarily possess a high amplitude emission or be present in sufficient concentration that the loss of integrated signal strength is not detrimental to signal detection.

The chemical composition of the microparticle can also vary as it can be made of any material accepted in the art, e.g., glass, ceramics, metal, silica, resin, latex, any plastic polymeric materials comprising polyurethane or polymerizable monomers selected from a group consisting of styrene, bromostyrene, acrylic acid, acrylonitrile, acrylamide, methyl methacrylate, vinyl chloride, vinyl benzyl chloride, vinyl acetate, vinyl toluene, vinyl pyridine, vinylidene chloride, divinyl benzene, butadiene, and isoprene as long as the reference protein can be covalently linked to the surface.

Covalent binding can be achieved via epoxy, aldehyde, carbodiimide, or any other known suitable linking method. The reactant for analyte detection can be immobilized on the solid particulate either directly or indirectly. The microparticles are modified for covalent coupling and reacted with the soluble reactant or probe. There are a number of ways to modify solid supports for the covalent immobilization of biomolecules. Surface modification can be accomplished by a variety of chemical and physical approaches including but not limited to the following: Addition of amino groups by fuming of nitrous acid; Bromoacetylation; Oxidation by use of plasma, ultraviolet (UV) light, or electron beams as energy sources in the presence of oxygen and air; Chemical grafting; Glutaraldehyde coating; Latex paint coating; Noncovalent attachment of an affinity spacer to aromatic groups among other methods. Selection of the proper spacer group (length, polarity, etc.) allows covalent immobilization of biomolecules on most plastic surfaces. Hydrophilic spacers shield the biomolecule from the aromatic, hydrophobic surface, greatly reducing nonspecific adsorption (background signal) and biomolecule inactivation over time. One can use BSI Corp.'s (Eden Prairie, Minn.) photochemical modification technology or Corning Costar (Kennebunk, Me.) polystyrene covalent immobilization of biomolecules. This covalent attachment of reactive groups produces the following four very stable surfaces: the N-oxysuccinimide (NOS) surface that covalently couples to amine groups; the maleimide surface for covalently coupling sulfhydryl groups; the hydrazide surface that is reactive toward periodate-activated carbohydrates. The NOS surface is useful for binding small antigens, peptides, enzymes, and aminated DNA. Use of the NOS-activated surface minimizes the challenges associated with immobilization of DNA for use in DNA probe assays. This surface is shown to immobilize 5' amine-modified oligonucleotides (oligos), providing an ideal template for hybridization and amplification. The DNA is bound at one end rather than at numerous sites along the molecule which results in high specificity and extremely low background. The typical covalent immobilization of a synthetic oligo, aminated at the 5' end via a C6 linker, to the NOS surface is as follows: the oligonucleotide is immobilized for 1 hour at 37° C. in 50-mM phosphate buffer (pH 8.5) containing 1-mM ethylene diamine tetraacetic acid (EDTA). After the beads are washed three times with 100-mM Tris (pH 7.5) and 150-mM NaCl, the unreactive NOS groups are blocked with 10-mM Tris and 1-mM EDTA buffer for 30 minutes at 37° C. The results indicate that there is a tenfold increase in absorbance for DNA covalently bound to the NOS surface as compared with that which is passively bound to a raw polystyrene surface. Hybridization is more efficient when the capture probe is covalently bound, suggesting that NOS-immobilized oligos are better suitable for the rapid detection of DNA in diagnostic assays.

Sample preparation for the maleimide surface involves the simple reduction of disulfide bonds between two cysteine residues on a protein by use of a mild reducing agent, such as dithiothreitol, 2-mercaptoethanol or tris(2-carboxyethyl) phosphine hydrochloride. The modification of primary amine groups with 2-iminothiolane hydrochloride (Traut's reagent) to introduce sulfhydryl groups is an alternative for biomolecules lacking them. Free sulfhydryls are immobilized to the maleimide surface.

The maleimide surface is tested for the site-specific immobilization of sulfhydryl groups by using a goat IgG Fc fragment, either unmodified or modified with Traut's reagent. There is a clear indication of sulfhydryl-specific immobilization on the maleimide surface. Results show a sevenfold increase in absorbance for Traut's modified Fc as compared to unmodified Fc.

The hydrazide surface is designed for covalent coupling of periodate-activated carbohydrates or glycosylated biomolecules. This surface proved beneficial for the site-specific immobilization of antibodies, carbohydrates, glycolipids, glycoproteins, and many enzymes. The hydrazide surface is tested for the site-specific immobilization of periodate-activated carbohydrates by immobilization of alkaline phosphatase, a glycoprotein that does not readily adsorb to raw polystyrene. Binding of periodate-activated alkaline phosphatase to the hydrazide surface is 16 times that of nonactivated alkaline phosphatase. The amount of alkaline phosphatase covalently bound to the hydrazide surface is also considerably more than can be passively bound to the high-binding surface.

While the covalent coupling method is a preferred method of reactant attachment, other methods of attachment, e.g., adsorption, hydrogen or ionic bonding are acceptable and are well known in the art. One popular means to immobilize any molecule possessing aliphatic carbon-hydrogen bonds is via UV illumination. Although the linkage is nonspecific and does not allow for site-directed orientation of a biomolecule, this surface is useful for the covalent immobilization of cell lysates, antigens of unknown structure, double-stranded DNA, and nonproteinaceous molecules, such as lipids.

The invention described herein is further exemplified in the following Examples. While these Examples provide a variety of combinations useful in performing the methods of the invention, they are illustrative only in regard to some of materials useful in this invention and are not to be viewed as limiting in any manner the scope of the invention.

EXAMPLE 1

Labeling Oligonucleotide Probes

The probe design is dictated by the location of the polymorphism or mutation. Generally, the probe is designed so that the polymorphic site hybridizes near the center of the probe. This is because mismatches near the ends of oligonucleotides tend not to be as disruptive to hybridization. Probe melting temperatures ($T_m$) are estimated by standard procedures like Primer Express™ primer design software (PE Applied Biosystems), which uses the "nearest neighbor" algorithm. A separate probe must be synthesized for each of the two alleles, one labeled with one fluorescent dye and the other labeled with another fluorescent. The length of each probe is adjusted so that both probes have a similar estimated Tm. One specific requirement for fluorogenic probes is that there be no G at the 5' end. This is because a G adjacent to the reporter dye quenches reporter fluorescence somewhat even after cleavage. Finally, probes can be derived from either strand.

Molecular beacons are a new class of oligonucleotides that can report the presence of specific nucleic acids (U.S. Pat. No. 5,925,517 to Tyagi et al.,). Molecular beacons emit an intense fluorescent signal only when hybridized to their target molecules. Generally, ssDNA molecular beacon contains a fluorophore of choice and (4-dimethylamino-phenylazo)benzoic acid (DABCYL) or variants thereof, like DABSYL, DABMI and Methyl Red as the quencher.

In another embodiment of a self-quenching probe, 6-carboxyfluorescein (6-FAM) is used as the reporter and 6-carboxytetramethylrhodamine (TAMRA) is used as the quencher such that the TAMRA dye substantially quenches any fluorescent emissions by 6-FAM. The fluorescent group is selected from the group consisting of fluorescein, tetramethylrhodamine, Texas Red, BODIPY, 5-[(2-aminoethyl)amino]napthalene-1-sulfonic acid (EDANS), Lucifer yellow, and coumarin. Probes containing reporter-quencher pairs ("TaqMan.R™", exonuclease assay) that are cleaved during amplification to release a fluorescent signal that is proportional to the amount of double stranded DNA present. The polymerase that conducts primer extension and amplifies the polynucleotide also possesses a 5'.fwdarw.3' exonuclease activity that serves to cleave the probe. In the exonuclease assay, a "reporter" dye and a "quencher" dye are attached to an oligonucleotide probe which is complementary to the target DNA. The dyes are selected and arranged to interact through a fluorescence resonance energy transfer (FRET) process. The reporter is a luminescent compound that can be excited either by chemical reaction, producing chemiluminescence, or by light absorption, producing fluorescence.

The quencher can interact with the reporter to alter its light emission, usually resulting in the decreased emission efficiency of the reporter. This phenomenon is called quenching. The efficiency of quenching is a strong function of the distance between the reporter molecule and the quencher molecule. Thus, in a nucleic acid hybridization assay, detection of a hybridization event is accomplished by designing an energy transfer system in which the spacing between a reporter and a quencher is modulated as a result of the hybridization. Two examples of systems that perform the exonuclease assay and other quantitation, fluorescent-based arrays are the ABI PRISM.TM. 7700 and ABI PRISM.TM. 7200 Sequence Detection Systems (Perkin-Elmer).

The molecular beacons are publicly available and can purchased from commercial companies like Biosearch Technologies (www.solidphase.com); Eurogentec (www.eurogentec.be); Gene Link (www.genelink.com); Integrated DNA Technologies (www.idtdna.com); Isogen Biosience; Life Technologies; Midland Certified Reagents; Operon Technologies; Oswel (Eurogentec); Research Genetics; Stratagene; Synthegen; Synthetic Genetics; TIB MOLBIOL; TriLink BioTechnologies;

In order to detect multiple targets in the same solution, molecular beacons can be made in many different colors utilizing a broad range of fluorophores. DABCYL, a non-fluorescent chromophore, serves as the universal quencher for any fluorophore in molecular beacons. Because of these properties, molecular beacons have been used for detection of RNAs within living cells (Matsuo, 1998 and Sokol et al. 1998), for monitoring the synthesis of specific nucleic acids in sealed reaction vessels (Tyagi, Bratu and Kramer 1998 and Leone et al. 1998), for homogenous one-tube assays for genotyping single-nucleotide variations in DNA (Piatek et al. 1998, Kostrikis et al. 1998, Giesendorf et al. 1998, Marras, Kramer and Tyagi, 1999) and for multiplex PCR for the detection of four pathogenic retroviruses (Vet et al. 1999).

Synthesis and purification of molecular beacons: The starting material for the synthesis of molecular beacons is an oligonucleotide that contains a sulfhydryl group at its 5'-end and a primary amino group at its 3'-end. DABCYL is coupled to the primary amino group utilizing an amine-reactive derivative of DABCYL. The oligonucleotides that are coupled to DABCYL are then purified. The protective trityl moiety is then removed from the 5'-sulfhydryl group and a fluorophore is introduced in its place using an iodoacetamide derivative. Recently a control pore column that can introduce DABCYL moiety at the 3' end of an oligonucleotide has become available which makes it possible to synthesize a molecular beacon completely on a DNA synthesizer. The sequence of the molecular beacon used throughout this protocol is: fluorescein-5'-probe-3'-DABCYL (see following example for specific sequences of possible probes).

Coupling of DABCYL: Dissolve 50-250 nmoles dry oligonucleotide in 500 µl of 0.1 M sodium bicarbonate, pH 8.5. Dissolve about 20 mg DABCYL (4-(4'-dimethylaminophenylazo)benzoic acid) succinimidyl ester (Molecular Probes) in 100 µl N,N-dimethylformamide and add to a stirring solution of the oligonucleotide in 10-µl aliquots at 20 min intervals. Continue stirring for at least 12 hours. Remove particulate material by spinning the mixture in a microcentrifuge for one min at 10,000 rpm. In order to remove unreacted DABCYL, pass the supernatant through a gel-exclusion column. Equilibrate a Sephadex G-25 column (NAP-5, Pharmacia) with buffer A, load the supernatant and elute with 1 ml buffer A. Filter the eluate through a 0.2 µm filter (Centrex MF-0.4, Schleicher & Schuell) before loading on the HPLC column. Purify the oligonucleotides on a C-18 reverse phase column (Waters) utilizing a linear elution gradient of 20 to 70% buffer B in buffer A and run for 25 min at a flow rate of 1 m/min. Monitor the absorption of the elution stream at 260 nm and 491 nm. Collect the peak that absorbs in both wavelengths and contains oligonucleotides with a protected sulfhydryl group at their 5'-end and DABCYL at their 3'-end. Precipitate the collected material with ethanol and salt, and spin in a centrifuge for 10 min at 10,000 rpm, discard the supernatant, dry the pellet and dissolve it in 250 µl buffer A.

Coupling of fluorophore: In order to remove the trityl moiety add 10 µl of 0.15 M silver nitrate and incubate for 30 min. Add 15 µl of 0.15 M DTT to this mixture and shake for 5 min. Spin for 2 min at 10,000 rpm and transfer the supernatant to a new tube. Dissolve about 40 mg 5-iodoactamidofluorescein (Molecular Probes) in 250 µl of 0.2 M sodium bicarbonate, pH 9.0 and add it to the supernatant. Incubate the mixture for 90 min. Each of these solutions should be prepared just before use. Remove the excess of fluorescein from the reaction mixture by gel exclusion chromatography and purify the oligonucleotides coupled to fluorescein by HPLC, following the instructions in steps 2 and 3 of the previous DABCYL example. Collect the fractions corresponding to peak, which absorb at wavelengths 260 nm and 491 nm and are fluorescent when observed with a UV lamp in a dark room. If a different fluorophore is coupled in place of fluorescein, its maximum absorption wavelength should be used instead of 491 nm. Precipitate the collected material and dissolve the pellet in 100 µl TE buffer. Determine the absorbance at 260 nm and estimate the yield (1 OD260=33 µg/ml).

Automated synthesis: Use a controlled pore glass column to introduce DABCYL (Glen Research) at the 3'-end of the oligonucleotide during the automated synthesis. At the 5' end of the oligonucleotide either a thiol or an amino modifier can be introduced for a subsequent coupling to the fluorophore, or the fluorophore can directly be introduced during the automated synthesis using a phosphoramidite. The 5' modifiers and fluorophores should remained protected with a trityl moiety during the synthesis.

Perform the post-synthesis steps as recommended by the manufacturer of the DNA synthesizer. Dissolve the oligonucleotide in 600 µl Buffer A. When the fluorophore is to be introduced manually, purify the oligonucleotide protected with trityl moiety. Remove the trityl moiety from the purified oligonucleotide and continue with the coupling of the fluorophore as described before. When a 5'-fluorophore is introduced via automated synthesis, purify the oligonucleotide protected with trityl moiety and remove the trityl moiety from the purified oligonucleotide. Precipitate the molecular beacon with ethanol and salt and dissolve the pellet in 100 µl TE buffer. Determine the absorbance at 260 m and estimate the yield.

EXAMPLE 2

Alternative Labeling Approaches

Random prime labeling is a common method for labeling nucleic acids. This technique relies on a mixture of random primers, usually six to 10 nucleotides long, to prime DNA synthesis in vitro along any double-stranded DNA template. The Klenow fragment of DNA polymerase I is the enzyme used most frequently to synthesize the labeled DNA, but some novel polymerases are also available. Developed initially using 32P-dATP or 32P-dCTP, random prime labeling can also incorporate nucleotides tagged with 3H, 35S, 33P, and 125I into the newly synthesized probes. Nonradioactive nucleotides such as fluorescein-11-dUTP or biotin-14-dCTP are preferable labels. End-labeling reactions designed to attach tagged nucleotides to DNA, RNA, or oligonucleotides form the basis of several commercially available products. Terminal deoxynucleotidyl transferase labels nucleic acids at the 3' end and is included in many products developed primarily for labeling oligonucleotides. Bacteriophage T4 polynucleotide kinase (PNK) can catalyze the transfer of the tag to the 5' terminus of DNA, RNA, or oligonucleotides, producing labeled products. Additionally, PNK quantitatively phosphorylates 5' ends using unlabeled ATP. The phage polymerases SP6, T7, and T3 are the most widely used for the generation of in vitro transcripts containing radioactive or nonisotopic labels. These probes offer greater sensitivity than DNA probes because RNA:RNA and RNA:DNA hybrids are more stable than DNA:DNA hybrids.

The polymerase chain reaction (PCR) has also found application in the generation of labeled DNA probes. One skilled in the art can easily use PCR-based labeling kits for amplifying radiolabeled, biotinylated, and digoxigenin (DIG)-labeled probes from small amounts of starting material as sold for example by Ambion, KPL, and Roche Molecular Biochemicals. Roche Molecular Biochemicals labeling system based on digoxigenin, a steroid hapten found in Digitalis plants. This system avoids the endogenous background problems encountered with biotin and other methods. Digoxigenin is readily incorporated into nucleic acids using enzymatic labeling methods and is detected with enzyme-labeled anti-DIG antibodies. Biotin is another popular nonisotopic alternative that is readily incorporated into nucleic acids enzymatically. For example, KPL's Detector™ nucleic acid probe labeling kits include a biotinylation quantitation standard for determining the relative specific activity of the labeled probe. This enables the user to optimize the amount of probe needed and thus minimizes background problems. New England Biolabs' NEBlot Phototope Kit uses random biotinylated octomers to prime in vitro synthesis from denatured double-stranded DNA and incorporates biotinylated dATP to provide sensitive nucleic acid detection. Regardless of the type of nonisotopic label used, nonradioactive probes have advantages over radioactive ones. While offering comparable sensitivity, nonisotopic probes do not decay and can be stored for at least one year. Frequently, kits for nonisotopic labeling are part of larger detection systems featuring enzyme-labeled streptavidin or anti-DIG antibodies, for example, which are visualized by colorimetric or chemiluminescent substrates. One skilled in the art can readily adapt any of these methods for carrying the preferred embodiment of the present invention.

Direct Labeling Methods: Some of nonisotopic labeling of nucleic acids do not rely on enzyme-mediated reactions. Unlike random prime labeling and nick translation, most of the direct labeling methods generate full-length, intact, labeled probes and are available commercially. The Label IT® Nucleic Acid Labeling Kits produced by Mirus Corp. and distributed by PanVera Corp. of Madison, Wis., covalently attach fluorescent dyes like rhodanine, fluorescein, biotin, digoxin, Cy3™, Cy5™, or DNP (dinitrophenol) to non-base pairing regions of guanine residues in any nucleic acid. Probes are labeled in a single step with rapid cleanup. The probes generated by these means are appropriate for use in instant invention. One of ordinary skill in the art can easily adapt the principles of present invention to other applications like fluorescence in situ hybridization (FISH), hybridization reactions, dot or slot blots, DNA transport studies, and microarray analysis.

In another approach one can use a platinum moiety that acts as a linker between the nucleic acid and the hapten. This approach is the basis of commercial The VersiTag Labeling Systems from NEN Life Science Products Inc. of Boston which labels nucleic acids directly with DNP or fluorescein. Ambion of Austin, Tex., offers the BrightStar™ Psoralen-Biotin kit consisting of the intercalating agent psoralen covalently bound to biotin. The psoralen-biotin reagent intercalates into the nucleic acid and is then covalently bound by exposure to UV light. In this way one can label RNA, DNA, PCR products, cDNA, and oligonucleotides in less than one hour. The Biotin Chem-Link and DIG Chem-Link Labeling kits from Roche Molecular Biochemicals of Indianapolis use the cis-platinum Chem-Link reagent to attach biotin or DIG to the N7 position of guanine and adenine bases. The simple reaction occurs in 30 minutes at 85° C. Amersham Pharmacia Biotech of Uppsala, Sweden, sells the AlkPhos Direct Labelling and Detection System for direct labeling of DNA, RNA, and oligonucleotides with alkaline phosphatase. Similarly, the ECL Direct Nucleic Acid Labeling and Detection System can directly label DNA or RNA probes with horseradish peroxidase (HRP). The procedure entails a 20-minute reaction, and detection is achieved by the HRP-catalyzed breakdown of luminol as source of luminescent light. Without limiting to these examples one can easily adapt Nick Translation Kits from Vysis Inc. of Downers Grove, Ill., to label probes with fluorescent tags originally designed for use in FISH and genomic microarray experiments. GenHunter Corporation of Nashville, Tenn., offers the ReversePrime™ cDNA Labeling Kit for preparing labeled cDNA probes for use in "reverse northern" blots. Its HotPrime™ DNA Labeling Kit is optimized for labeling differential display fragments but can label other DNA probes as efficiently as any other publicly available means.

Nucleic acid probes that have hybridized to their target sequence are detected based on various methods that introduce a detectable chemiluminescent, fluorescent or other identifiable optical label into a nucleic acid probe. Several of these techniques are described in U.S. Pat. Nos. 4,968,602, 4,818,680, 5,104,791, and 5,272,056, and foreign applications WO91/00926 and GB2169403A. Other means and methods for detecting and quantifying biological samples are known such as for example disclosed in U.S. Pat. Nos. 6,059,561, 6,027,898, and 5,891,656.

U.S. Pat. Nos. 5,283,174 and 6,063,574 describe for example the use of a chemiluminescent label with DNA probes. The label is composed of an acridinium ester or dioxetane and has a number of desirable properties. It is stable to hybridization conditions, light is emitted only upon exposure to an enzyme or alkaline peroxide, the emission kinetics are rapid, and the label on the unhybridized probe can be destroyed without an impact on the signal generated by hybridized probe.

U.S. Pat. Nos. 5,089,387 and 6,060,237 describe a diffraction assay for the detection of DNA hybridization. In these inventions, a solid support, generally silicon or polysilicon, is coated with a DNA probe. The diffraction property of the surface is altered upon addition of the analyte to the surface. The angle of diffraction is a function of the wavelength of incident light and the density and spacing of the analyte on the surface. A single detector or a multiple detector array is used to detect and measure the diffracted light and presence of the analyte.

In yet another approach primers immobilized on fluorescently addressable microspheres are allowed to anneal to the DNA strand of the analyte under investigation, and are subsequently extended by either DNA polymerase using fluorescent dideoxynucleotides or ligated by DNA ligase to fluorescent reporter oligonucleotides. The fluorescence of either the dideoxynucleotide or the reporter (secondary reagent) oligonucleotide attached to the immobilized primer is measured by flow cytometry, thereby identifying the nucleotide polymorphism on the DNA strand of analyte.

It is thus clear that concrete means for labeling probes and/or analyte and subsequent detection are almost infinite and one skilled in the art can easily choose one or another means as suitable for the purpose of this invention.

EXAMPLE 3

Detection of Sequence (Allele) Variations in a Nucleic Acid Sample

The method of the invention, which can be used to detect sequence variations in any nucleic acid sample, is demonstrated for the purpose of illustration, in the example set forth for the human BRCA1 gene. The BRCA1 gene is approximately 100,000 base pairs of genomic DNA encoding the 1836 amino acid BRCA1 protein. The sequence is divided into 24 separate exons. Exons 1 and 4 are noncoding and are not part of the final functional BRCA1 protein product. Each exon consists of 200-400 bp, except for exon 11 which contains about 3600 bp. The sequence for the coding region of the human BRCA1 gene can be found in GENBANK (e.g., AF005068 [gi:2218153]) or in the U.S. Pat. No. 6,048,689.

White blood cells are collected from the patient and genomic DNA is extracted according to well-known methods. The genomic DNA is used as a template to amplify a separate DNA fragment encompassing the site of each of the eight mutations to be tested. Each PCR reaction contains the following components: 1 microliter template (100 ng/microliter) DNA, 5.0 microliter 10× PCR Buffer (Perkin-Elmer), 5.0 microliter dNTP (2 mM each dATP, dCTP, dGTP, dTTP), 5.0 microliter Forward Primer (10 microM), 5.0 microliter Reverse Primer (10 mM), 0.5 microliter Taq DNA Polymerase (Perkin-Elmer). 25 mM MgCl2 is added to each reaction and H2O is added to 50 microliter. All reagents for each exon except the genomic DNA can be combined in a master mix and aliquoted into the reaction tubes as a pooled mixture. For each exon analyzed for mutations, the following control PCRs are set up: "Negative" DNA control (100 ng placental DNA (Oncor, Inc., Gaithersburg, Md.); and three "no template" controls. PCR for all exons is performed using the appropriate thermocycling conditions. The quality of the PCR products are examined prior to further analysis by electrophoresing an aliquot of each PCR reaction sample on an agarose gel. 5 microliter of each PCR reaction is run on an agarose gel alongside a DNA mass ladder (Gibco BRL Low DNA Mass Ladder).

The electrophoresed PCR products are analyzed according to the following criteria: Each patient sample must show a single band of the corresponding size as expected theoretically. If a patient sample demonstrates smearing or multiple bands, the PCR reaction must be repeated until a clean, single band is detected. However, the exceptions to this are for example the mutations 1294del40 and T>Gins59 (the term "del" stands for deletion and the term "ins" stands for inserion). If a patient sample from one of these two exons (11B and 6, respectively) demonstrates two bands instead of one, it may indicate the presence of the mutation. The 1294del40 mutation shortens the size of the corresponding PCR product by 40 bp and the T>Gins59 mutation lengthens the size of the corresponding PCR product by 59 bp. Obviously, patients heterozygous for these mutations would have a normal sized PCR product from the normal allele, and an altered sized PCR product from the mutant allele. If no PCR product is visible or if only a weak band is visible, but the control reactions with placental DNA template produced a clear band, the patient sample should be re-amplified with 2 times as much template DNA. All three "no template" reactions must show no amplification products. Any PCR product present in these reactions is the result of contamination. If any one of the "no template" reactions shows contamination, all PCR products should be discarded and the entire PCR set of reactions should be repeated after the appropriate PCR decontamination procedures have been taken.

Once the optimal conditions are identified there is no critical need for further controls as described above and patient samples can be processed and analyzed directly according to the various preferred embodiments of the invention. The probes are labeled as shown in the example supra.

Any of these probes is bound to the fluorescently addressable beads and according to the preferred embodiment two probes (typically mutant and normal allele combinations) are bound to the same bead at the same time. One clearly can bind more then two probes to the same bead provided that each individual probe is distinguishable from another either by color or fluorescence intensity (see FIG. 1). Thus for example one can attach simultaneously 185delAG normal-mutant pair and T300G normal-mutant pair to the same bead as long as these two pairs are distinguishable. All is required is that fluorescent dyes are selected in appropriate manner and means of detection, i.e., flow cytometer, is capable of differentiating pairs and individual members of said pairs.

TABLE 1

BRCA1 allele specific nucleotide probes

| | |
|---|---|
| 185delAG-Mutant | 5'-ATC TTA GTG TCC CAA AT-3' |
| 185delAG-Normal | 5'-AAT CTT AGA GTG TCC CA-3' |
| T300G-Mutant | 5'-CTT CAC AGG GTC CTT TA-3' |
| T300G-Normal | 5'-CTT CAC AGT GTC CTT TA-3' |
| T>G-Mutant | 5'-TCA AAC AAG TTA ATT TC-3' |
| T>G-Normal | 5'-TCA AAC ATT TTA ATT TC-3' |
| 1136insA-Mutant | 5'-CAG AAA AAA AAG GTA GA-3' |
| 1136insA-Normal | 5'-CAG AAA AAA AGG TAG AT-3' |
| 1294del40-Mutant | 5'-GTG ATG AAC AAA TGC CA-3' |
| 1294delL40-Normal | 5'-GAT GAC TCA CAT GAT GC-3' |
| 4184del4-Mutant | 5'-AGA AAA TAA GAA GAG CA-3' |
| 4184del4-Normal | 5'-AGA AAA TAA TCA AGA AG-3' |
| C4446T-Mutant | 5'-AGG ACC TGT GAA ATC CA-3' |
| C4446T-Normal | 5'-AGG ACC TGC GAA ATC CA-3' |
| 5382insC-Mutant | 5'-AGA GAA TCC CCA GGA CA-3' |
| 5382insC-Normal | 5'-AGA GAA TCC CAG GAC AG-3' |

To denature the DNA the PCR products are briefly heated to 95 degrees C. for 5 minutes, and immediately placed on ice. The samples containing analytes are mixed with microspheres having labeled probes and hybridized at 52 degrees C. with moderate shaking. The optimal stringency conditions are found experimentally and to assure higher specificity of probe binding they are preferably stringent conditions. Following hybridization, the probe mix is decanted and washed in 2× SSC, 0.1% SDS for 20 minutes at 65 degree C. or used directly without washing for flow cytometry analysis.

The phrases "hybridizing specifically to" or "specific hybridization" or "selectively hybridize to", refer to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization experiments such as Southern and Northern hybridizations are sequence dependent, and are different under different environmental parameters. An extensive guide to the hybridization of nucleic acids is found for example in U.S. Pat. No. 6,066,453 incorporated herein by reference.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe.

Very stringent conditions are selected to be equal to the Tm for a particular probe.

EXAMPLE 4

Standard Protocols for Nucleic Acid Amplification

Nucleic acids, e.g., DNA or RNA in the sample of interest can be amplified prior to detection steps according to standard procedures well known in the art. These techniques include but are not limited to polymerase chain reaction (PCR), strand displacement amplification (SDA), transcription mediated amplification (TMA), ligase chain reaction (LCR), nucleic acid sequence based amplification (NASBA), self-sustained sequence based amplification (3SR), Target Nucleic Acid Amplification/Detection, rolling circle amplification, amplification of RNA by an RNA-directed RNA polymerase and the like.

Amplifications are generally of two types: first is well known PCR-like based amplifications based on use of thermophylic enzymes and the second is isothermic amplification which does not require extreme temperature variations. Representative protocol for isothermic process is, for example, the isothermal Self-Sustained Sequence Amplification (3SR) protocol. General 3SR reaction conditions comprise: 40 mM Tris-Cl pH 8.1, 20 mM $MgCl_2$, 25 mM NaCl, 2 mM spermidine hydrochloride, 5 mM dithiothreitol, bovine serum albumin (80 microg/ml), 1 mM dNTPs, 4 MM rNTPs, 250 ng T7 promoter/gene-specific chimeric downstream oligonucleotide, 250 ng gene specific upstream oligonucleotide, 30 units AMV reverse transcriptase, 100 units T7 RNA polymerase, 4 units RNAse H, and template RNA in a final volume of 100 microliter, incubated at 37 degrees C. for 1 hour. Products are electrophoresed on 5% polyacrylamide/7M urea denaturing gels, stained with 1 microg/ml ethidium bromide and visualized under 300 nm ultraviolet light. After establishing primer pairs for individual targets function in individual 3SR reactions, both pairs of primers are added to a single reaction. The products are evaluated by gel electrophoresis as described above.

EXAMPLE 5

Measuring Multiple Protein Variants

Human chorionic gonadotropin (hCG) is produced by placenta during pregnancy and by some tumor cells. However, multiple hCG-related molecules are present in pregnancy serum and urine samples. These include so-called non-nicked hCG, nicked hCG, hyper- and hypoglycosylated hCG, hCG missing the C-terminal extension, free alpha-subunit, large free alpha-subunit, free beta-subunit, nicked free beta-subunit, and beta-core fragment. Over 100 immunoassays are sold for identifying and quantifying hCG-related molecules in serum or urine. Each measures non-nicked hCG and one of seven combinations of the other hCG-related molecules. While these assays are valid by themselves it is difficult to reconcile the inter-assay discordance in hCG determinations. Whereas minor variations are noted in different kit results in normal pregnancy samples (about twofold variation), much larger variations may be found in two immunoassay results from irregular gestations, e.g., spontaneous abortion, aneuploidy, preeclampsia, cancers, and trophoblast disease. It is thus difficult to choose an ideal assay and there is no assay that exists currently which will measure all possible variations simultaneously.

The present invention provides a feasible approach to solve this and related problems in the field of immunoassays requiring the analysis of multiple analytes using a limited number of fluorescently addressable microspheres.

The general method of binding a reactant, e.g., antibody or antigen to a microsphere and conducting analyte detection assays is disclosed in commonly owned U.S. Pat. No. 5,981,180 incorporated herein by way of reference. In the prior art it was required that the bead set "AA" had to carry an antibody against alpha chain of hCG and bead set "BB" had carry an antibody against beta chain of hCG, meaning that two sets were required for the analysis. The inventive step provides a single set of beads carrying the mixture of antibodies against both alpha and beta chains of hCG, which detects dimer or "holo" form of hCG consisting of both alpha and beta chains simultaneously. As another example of the prior art the first set had to have antibody against truncated core region of beta hCG and the second set had to carry an antibody against C-terminal end of beta hCG. In contrast, the instant set of beads displays the mixture of these antibodies which bind intact beta chain having core and C-terminal region of hCG. The antibodies against hCG are readily available and one can easily select such antibodies from numerous commercial sources, e.g., Zymed Laboratories Inc., (South San Francisco, Calif.) or Research Diagnostics Inc., (Flanders, N.J.).

In a similar manner one can select any of analytes and variants thereof as listed supra. As a non-limiting example, is a situation when the analyte of interest is polypeptide, accordingly its variant is an epitope selected from the group consisting of IL-1, IL-2, IL-3, IL4, IL-5, IL-6, IL-7, IL-8, IL-9, IL-10, IL-11, IL-12, IFN-.alpha., IFN-beta., IFN-65, CD2, CD3, CD4, CD5, CD8, CD11a, CD11b, CD11c, CD16, CD18, CD21, CD28, CD32, CD34, CD35, CD40, CD44, CD45, CD54, CD56, K2, K1, P.beta., O.alpha., M.alpha., M.beta.2, M.beta.1, LMP1, TAP2, LMP7, TAP1, O.beta., IA.beta., IA.alpha., IE.beta., IE.beta.2, IE.alpha., CYP21, C4B, CYP21P, C4A, Bf, C2, HSP, G7a/b, TNF-.alpha., TNF-.beta., D, L, Qa, T1a, COL11A2, DP.beta.2, DP.alpha.2, DP.beta.1, DP.alpha.1, DN.alpha., DM.alpha., DM.beta., LMP2, TAPi1, LMP7, DO.beta., DQ.beta.2, DQ.alpha.2, DQ.beta.3, DQ.beta.1, DQ.alpha.1, DR.beta., DR.alpha., HSP-70, HLA-B, HLA-C, HLA-X, HLA-E, HLA-J, HLA-A, HLA-H, HLA-G, HLA-F, nerve growth factor, somatotropin, somatomedins, parathormone, FSH, LH, EGF, TSH THS-releasing factor, HGH, GRHR, PDGF, IGF-I, IGF-II, TGF-.beta., GM-CSF, M-CSF, G-CSF1, erythropoietin, 4-N-acetylgalactosaminyltransferase, GM2, GD2, GD3, MAGE-1, MAGE-2, MAGE-3, MUC-1, MUC-2, MUC-3, MUC-4, MUC-18, ICAM-1, C-CAM, V-CAM, ELAM, NM23, EGFR, E-cadherin, N-CAM, CEA, DCC, PSA, Her2-neu, UTAA, melanoma antigen p75, K19, HKer 8, pMel 17, tyrosinase related proteins 1 and 2, p97, p53, RB, APC, DCC, NF-1, NF-2, WT-1, MEN-I, MEN-II, BRCA1, VHL, FCC and MCC, ras, myc, neu, raf, erb, src, fms, jun, trk, ret, gsp, hst, bcl abl, C1q, C1r, C1s, C4, C2, Factor D, Factor B, properdin, C3, C5, C6, C7, C8, C9, C1Inh, Factor H, C4b-binding protein, DAF, membrane cofactor protein, anaphylatoxin inactivator S protein, HRF, MIRL, CR1, CR2, CR3, CR4, C3a/C4a receptor, C5a receptor, HIV (gag, pol, qp41, gp120, vif, tat, rev, nef, vpr, vpu, vpx), HSV (ribonucleotide reductase, .alpha.-TIF, ICP4, ICP8, ICP35, LAT-related proteins, gB, gC, gD, gE, gH, gI, gJ), influenza (hemagluttinin, neuraminidase, PB1, PB2, PA, NP, M.sub.1, M.sub.2, NS.sub.1, NS.sub.2), papillomaviruses (E1, E2, E3, E4, E5a, E5b, E6, E7, E8, L1, L2) adenovirus (E1A, E1B, E2, E3, E4, E5, L1, L2, L3, L4, L5), Epstein-Barr Virus (EBNA), Hepatitis B Virus (gp27.sup.S, gp36.sup.S, gp42.sup.S, p22.sup.c, pol, x) and Nuclear Matrix Proteins among others.

The technical details of how to perform the routine steps associated with this invention can be readily glanced from commonly owned issued U.S. Pat. Nos. 6,057,107; 6,046,807; 5,981,180; 5,736,330 and co-pending patent applications corresponding to published PCT applications WO 99/58958; WO 99/58955; WO 99/57955; WO 99/52708; WO 99/37814; WO 99/36564; WO 99/19515; WO 98/59233; WO 97/14028 hereby incorporated in their entirety by way of reference.

EXAMPLE 6

Dual Reporter Oligonucleotide Ligation Assay

This experiment shows as specific example of a detecting two alleles of target nucleic acid molecules of a genetic locus. For this experiment, the reactant is a capture probe complementary to a common sequence within the locus, and the reporter agents are reporter probes specific to the individual alleles, which reporter probes are distinctly labeled.

Figure 2:
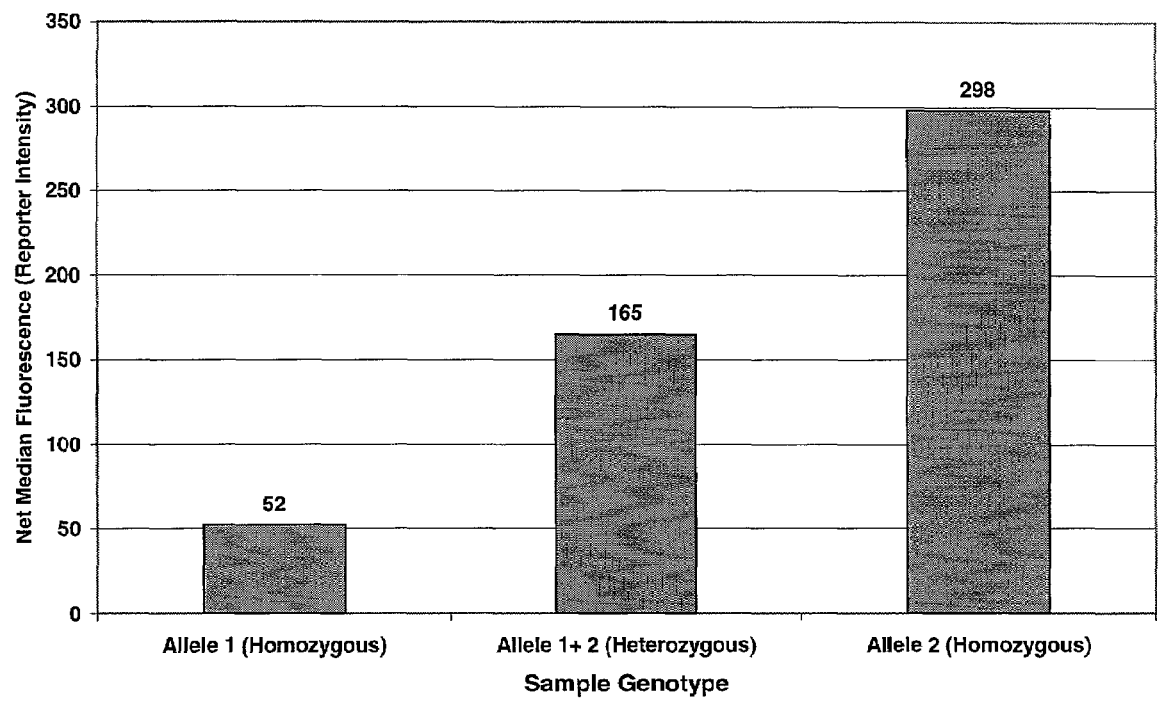
FIG. 2 illustrates a dual reporter read-out assay results using oligonucleotide ligation assay (OLA).

A population of fluorescently addressable microspheres is provied. A capture probe complementary to a common sequence within the queried target is covalently coupled to the microspheres. Oligonucleotide reporter probes complementary to the individual alleles are designed to carry either a Cy3 reporter (Allele 1) or phycoerythrin (PE) (Allele 2). The target sample is mixed with the capture probe-coupled beads and the two reporter probes. Standard oligonucleotide ligation assay procedure is then followed. Following ligation, the reaction mix is heated to denature the sample (to remove the genomic target from the bead complex) and the ligated samples are passed through an analyzer. Some exemplary data are shown in FIG. 2.

EXAMPLE 7

Diagnostic Kits

This invention also provides diagnostic kits for the detection of analytes and their variants. In a preferred embodiment, the kits include one or more sets of fluorescently addressable beads with predetermined reactants as disclosed supra. Examples of reactants include nucleic acid probes and antibodies or antigens. The kits can additionally include other reagents and instructional materials describing how to use the kit contents in detecting the analytes of interest. The kits can also include one or more of various labels or labeling agents (secondary reagents or reporter reagents) to facilitate the detection of the probes, reagents necessary for the hybridization or immunoassay including buffers, blocking agents, devices like disposable pipettes and the like, positive and negative controls and so forth.

While the invention has been described in connection with specific embodiments thereof, it will be understood that it is capable of further modifications and this application is intended to cover any variations, modifications, uses, or adaptations of the invention following, in general, the principles of the invention and including such departures from the present disclosure as come within known or customary practice within the art to which the invention pertains and as may be applied to the essential features herein before set forth and as follows in the scope of the appended claims. All publications, internet information from disclosed websites, and patent documents cited in this application are incorporated by reference in their entirety for all purposes to the same extent as if each individual publication or patent document were so individually denoted.

We claim:

1. A method for detection of different reactive sites on at least one analyte, the method comprising:
   (1) providing a population of microspheres, wherein each of the microspheres carries different reactants capable of reacting respectively with the different reactive sites, wherein the at least one analyte comprises a nucleic acid molecule, wherein the different reactive sites comprise one or more alleles of a locus on the nucleic acid molecule, and wherein the different reactants comprise one or more fluorescently-labeled nucleic acid probes respectively specific for the one or more alleles;
   (2) allowing the different reactants and the different reactive sites to react, thereby forming reactant-reactive site pairs on the microspheres, wherein different reactant-reactive site pairs are detectably distinguishable from each other by their fluorescence intensity, and wherein the different reactant-reactive site pairs are not detectably distinguishable from each other by their fluorescence wavelength; and
   (3) detecting the fluorescence intensity of the reactant-reactive site pairs formed on one of the microspheres simultaneously, whereby the presence or absence of each of the different reactive sites on the at least one analyte is determined based on the fluorescence intensity of the reactant-reactive site pairs.

2. The method of claim 1, wherein the fluorescence intensity of the reactant-reactive site pairs is detected using flow cytometry.

3. The method of claim 1, wherein the nucleic acid molecule has been subject to in vitro manipulation.

4. The method of claim 3, wherein the in vitro manipulation is a PCR amplification, a restriction enzyme digestion, strand displacement amplification (SDA), transcription mediated amplification (TMA), ligase chain reaction (LCR), nucleic acid sequence based amplification (NASBA), primer extension, rolling circle amplification, amplification of RNA by an RNA-directed RNA polymerase, or a combination thereof.

5. A method for determining allele zygosity of nucleic acid molecules of a genetic locus having two alleles, the method comprising:
   (1) providing a population of microspheres, wherein each of the microspheres carries two different nucleic acid probes respectively specific to each of the two alleles;
   (2) allowing the probes to hybridize to the two alleles, thereby forming allele-probe pairs on the microspheres, wherein different allele-probe pairs are detectably distinguishable by their fluorescence intensity, and wherein the different allele-probe pairs are not detectably distinguishable by their fluorescence wavelength; and
   (3) detecting the fluorescence intensity of the allele-probe pairs formed on one or the microspheres simultaneously, whereby the allele zygosity of the genetic locus is determined based on the fluorescence intensity of the allele-probe pairs.

6. A method for determining polymorphism of nucleic acid molecules of a genetic locus having multiple alleles, the method comprising:
   (1) providing a population of microspheres, wherein each of the microspheres carries multiple different nucleic acid probes respectively specific to each of the multiple alleles;
   (2) allowing the probes to hybridize to the multiple alleles, thereby forming allele-probe pairs on microspheres, wherein different allele-probe pairs are distinguishable by fluorescence intensity, and wherein the different allele-probe pairs are not distinguishable by fluorescence wavelength; and
   (3) detecting the fluorescence intensity of the allele-probe pairs formed on one of the microspheres simultaneously, whereby the allele polymorphism of the genetic locus is determined based on the fluorescence intensity of the allele-probe pairs.

7. The method of claim 6, wherein the genetic locus is the human BRCA1 gene.

8. The method of claim 6, wherein the nucleic acid molecules comprise a mixture of nucleic acid molecules from more than one organism.

9. A method for detecting different analytes in a sample, the method comprising:
(1) providing a population of microspheres, wherein each of the microspheres carries different reactants capable of reacting respectively to each of the different analytes;
(2) allowing the reactant and the analytes to react, thereby forming reactant-analyte pairs;
(3) providing a mixture of reporter reagents capable of reacting with the reactant-analyte pairs;
(4) allowing the reporter reagents to react with the reactant-analyte pairs to form reactant-analyte-reporter reagent complexes, wherein different reactant-analyte-reporter reagent complexes are distinguishable by fluorescence intensity, but not by fluorescence wavelength, wherein the analytes are alleles of target nucleic acid molecules of a genetic locus, wherein the reactants are capture probes complementary to a common sequence within the genetic locus, and wherein the reporter reagents are reporter probes specific to the individual alleles; and
(5) detecting the fluorescence intensity of the reactant-analyte-reporter reagent complexes formed on one of the microspheres simultaneously, whereby the presence or absence of each of the different analytes is determined based on the fluorescence intensity.

10. The method of claim 9, wherein the capture probes abut their respective reporter probes, wherein the reactant-analyte-reporter reagent complexes are formed via oligonucleotide ligation assay, and wherein the fluorescence intensity is analyzed using a flow cytometer.

11. The method of claim 9, further comprising heating the complexes to remove the target nucleic acid molecule between steps (4) and (5).

12. A method for detecting SNPs in target nucleic acid molecules, wherein each of the SNPs has two or more polymorphisms, the method comprising:
(1) providing a plurality of populations of microspheres, wherein each population corresponds to one of the SNPs and has an addressable signature, and wherein each of the microspheres in a population carries two or more nucleic acid probes specific respectively to each of the polymorphisms for the SNP;
(2) allowing the probes to hybridize to the SNPs, thereby forming SNP-probe pairs, wherein different SNP-probe pairs are distinguishable by fluorescence intensity but not by fluorescence wavelength; and
(3) determining the type of SNPs via detecting the fluorescence intensity of the SNP-probe pairs formed on one of the microspheres simultaneously, and detecting the addressable signature.

13. The method of claim 12, further comprising fragmenting the nucleic acid molecules.

14. A method for detecting different reactive sites on an analyte, comprising:
allowing different reactants to react with the different reactive sites on the analyte to form one or more reactant-reactive site pairs, wherein the different reactants are carried on a microsphere, and wherein each of the different reactants is capable of reacting specifically with one of the different reactive sites;
analyzing the microsphere to detect output signal responsive to each of the reactant-reactive site pairs, formed on the microsphere, wherein different reactant-reactive site pairs are distinguishable by their fluorescence intensity but not by their fluorescence wavelength;
determining which of the reactant-reactive site pairs were formed using the output signal; and
determining which of the different reactive sites are present on the analyte using results of said determining, wherein a determination that a reactant-reactive site pair was formed indicates a presence of the reactive site, corresponding to the formed reactant-reactive site pair, on the analyte.

15. The method of claim 14, wherein the different reactants are fluorescently-labeled.

16. The method of claim 14, wherein the different reactive sites are fluorescently-labeled.

17. The method of claim 14, wherein said analyzing is performed using flow cytometry.

18. The method of claim 14, wherein the analyte is a nucleic acid molecule, wherein the different reactive sites comprise two or more alleles of a locus on the nucleic acid molecule, and wherein the different reactants comprise two or more fluorescently-labeled nucleic acid probes respectively specific for the two or more alleles.

19. The method of claim 18, wherein the nucleic acid molecule has been subject to in vitro manipulation.

20. The method of claim 19, wherein the in vitro manipulation is a PCR amplification, a restriction enzyme digestion, strand displacement amplification (SDA), transcription mediated amplification (TMA), ligase chain reaction (LCR), nucleic acid sequence based amplification (NASBA) primer extension, rolling circle amplification, amplification of RNA by an RNA-directed RNA polymerase, or a combination thereof.

21. The method of claim 14, wherein the analyte is an antigen molecule, wherein the different reactive sites comprise two or more epitopes on the antigen molecule, and wherein the different reactants comprise two or more fluorescently-labeled antibodies respectively specific for the two or more epitopes.

22. The method of claim 14, wherein the analyte is a human chorionic gonadotropin (hCG) related molecule, wherein the different reactive sites comprise a alpha-subunit or a variant thereof or a beta-subunit or a variant thereof, and wherein the different reactants comprise a respective antibody.

23. A method for detecting different analytes in a sample, comprising:
allowing different reactants to react with the different analytes to form one or more reactant-analyte pairs, wherein the different reactants are carried on a microsphere, and wherein each of the different reactants are capable of reacting specifically with one of the different analytes;
allowing reporter reagents to react with the one or more reactant-analyte pairs to form reactant-analyte-reporter reagent complexes;
analyzing the microsphere to detect an output signal responsive to each of the complexes formed on the microsphere, wherein different complexes are distinguishable by their fluorescence intensity but not by their fluorescence wavelength;
determining which of the complexes were formed using the output signal; and
determining which of the different analytes are present in the sample using results of said determining, wherein a determination that a complex was formed indicates a presence of the analyte, corresponding to the formed complex, in the sample.

24. The method of claim 23, wherein the different analytes comprise immunoglobulins, wherein the different reactants comprise antigens that bind to the immunoglobulins, and wherein the reporter agents comprise fluorescently-labeled anti-immunoglobulin antibodies.

25. The method of claim 24, wherein the antigens comprise insulin.

26. The method of claim 23, wherein the different analytes comprise alleles of target nucleic acid molecules of a genetic locus, wherein the different reactants comprise capture probes complementary to a common sequence within the genetic locus, and wherein the reporter reagents comprise reporter probes specific to the individual alleles.

27. The method of claim 26, wherein the capture probes abut their respective reporter probes, wherein the reactant-analyte-reporter reagent complexes are formed via oligonucleotide ligation assay, and wherein the complexes are analyzed using a flow cytometer.

28. The method of claim 26, further comprising heating the complexes to remove the target nucleic acid molecules prior to said analyzing.

* * * * *